(12) United States Patent
Pavicic et al.

(10) Patent No.: US 11,532,801 B2
(45) Date of Patent: *Dec. 20, 2022

(54) ORGANIC ELECTROLUMINESCENT DEVICE COMPRISING A REDOX-DOPED ELECTRON TRANSPORT LAYER AND AN AUXILIARY ELECTRON TRANSPORT LAYER

(71) Applicants: Novaled GmbH, Dresden (DE); Samsung SDI Co. Ltd., Gyeonggi-do (KR)

(72) Inventors: Domagoj Pavicic, Dresden (DE); Jerome Ganier, Dresden (DE); Vygintas Jankus, Dresden (DE); Hyungsun Kim, Suwon-si (KR); Byungku Kim, Suwon-si (KR); Youngkwon Kim, Suwon-si (KR); Younhwan Kim, Suwon-si (KR); Hun Kim, Suwon-si (KR); Eun Sun Yu, Suwon-si (KR); Sung-Hyun Jung, Suwon-si (KR)

(73) Assignees: Novaled GmbH, Dresden (DE); Samsung SDI Co. Ltd., Gyeonggi-do (KR)

( * ) Notice: Subject to any disclaimer, the term of this patent is extended or adjusted under 35 U.S.C. 154(b) by 150 days.

This patent is subject to a terminal disclaimer.

(21) Appl. No.: 15/784,389

(22) Filed: Oct. 16, 2017

(65) Prior Publication Data
US 2018/0114940 A1    Apr. 26, 2018

(30) Foreign Application Priority Data
Oct. 24, 2016    (EP) .................................... 16195375

(51) Int. Cl.
*H01L 51/50*    (2006.01)
*C07D 221/18*    (2006.01)
(Continued)

(52) U.S. Cl.
CPC ........ *H01L 51/5076* (2013.01); *C07D 221/18* (2013.01); *C07D 239/70* (2013.01);
(Continued)

(58) Field of Classification Search
CPC ............ H01L 51/5076; H01L 51/0067; H01L 51/0072; H01L 51/0071; H01L 2251/554;
(Continued)

(56) References Cited

U.S. PATENT DOCUMENTS 8,283,054 B2 * 10/2012 Spindler ............. H01L 51/5278
428/690
8,431,046 B2    4/2013 Zeika et al.
(Continued)

FOREIGN PATENT DOCUMENTS

JP    2001-291593 A    10/2001
JP    2005068078 A *   3/2005
(Continued)

OTHER PUBLICATIONS

KR-20160095667-A—translation (Year: 2016).*
(Continued)

*Primary Examiner* — Dawn L Garrett
(74) *Attorney, Agent, or Firm* — Eversheds Sutherland (US) LLP

(57) ABSTRACT

The present invention relates to an organic electroluminescent device, particularly to an organic light emitting diode (OLED) including an ETL stack of at least two electron transport layers, wherein the first electron transport layer comprises a first electron transport matrix compound and the second electron transport layer comprises second electron
(Continued)

transport matrix compound and a redox n-dopant, and a device comprising the OLED.

11 Claims, 2 Drawing Sheets

(51) Int. Cl.
    *C07D 239/70*     (2006.01)
    *C07D 251/24*     (2006.01)
    *C07D 495/04*     (2006.01)
    *H01L 51/00*     (2006.01)

(52) U.S. Cl.
CPC ......... *C07D 251/24* (2013.01); *C07D 495/04* (2013.01); *H01L 51/0067* (2013.01); *H01L 51/0071* (2013.01); *H01L 51/0072* (2013.01); *H01L 51/508* (2013.01); *H01L 51/5012* (2013.01); *H01L 51/0054* (2013.01); *H01L 51/0061* (2013.01); *H01L 51/0073* (2013.01); *H01L 2251/301* (2013.01); *H01L 2251/533* (2013.01); *H01L 2251/554* (2013.01)

(58) Field of Classification Search
CPC . H01L 51/5092; H01L 51/508; H01L 51/506; H01L 51/0032; H01L 51/5012; H01L 51/0073; H01L 51/0061; H01L 51/0054; H01L 2251/533; H01L 2251/301; H01L 51/001; H01L 51/0034; H01L 51/0045; H01L 51/005; H01L 51/0075; H01L 51/0077; H01L 51/0093; H01L 51/0094; H01L 51/0095; H01L 51/5024; H01L 51/5028; H01L 51/5036; H01L 51/504; C09K 11/06; C07D 239/70; C07D 221/18; C07D 495/04; C07D 251/24; C07D 219/00; C07D 219/02; C07D 221/02
See application file for complete search history.

(56) References Cited

U.S. PATENT DOCUMENTS

| | | | |
|---|---|---|---|
| 9,118,019 B2 | 8/2015 | Limmert et al. | |
| 9,502,660 B2 | 11/2016 | Dorak et al. | |
| 2003/0165711 A1 | 9/2003 | Kim et al. | |
| 2008/0122344 A1* | 5/2008 | Shin | H01L 51/0072 313/504 |
| 2010/0288362 A1* | 11/2010 | Hatwar | H01L 51/5044 136/263 |
| 2012/0286253 A1* | 11/2012 | Schmid | H01L 51/0067 257/40 |
| 2014/0151670 A1* | 6/2014 | Lee | H01L 51/0052 257/40 |
| 2017/0309830 A1 | 10/2017 | Kim et al. | |
| 2019/0058123 A1* | 2/2019 | Pavicic | H01L 51/0071 |

FOREIGN PATENT DOCUMENTS

| | | | | |
|---|---|---|---|---|
| JP | 2008-195623 A | | 8/2008 | |
| KR | 20160095667 A | * | 8/2016 | |
| WO | WO-03007658 A2 | * | 1/2003 | ............. C07C 13/62 |
| WO | 2007/107356 A1 | | 9/2007 | |
| WO | WO-2009054253 A1 | * | 4/2009 | ........... C07D 239/26 |
| WO | 2011/154131 A1 | | 12/2011 | |
| WO | WO-2012175219 A1 | * | 12/2012 | ............. C07F 9/065 |
| WO | 2013/079217 A1 | | 6/2013 | |
| WO | 2013/079676 A1 | | 6/2013 | |
| WO | 2013/079678 A1 | | 6/2013 | |

OTHER PUBLICATIONS

JP-2005068078-A—translation (Year: 2005).*
WO-2009054253-A1—translation (Year: 2009).*
Chem. Mat., (2000), 12, pp. 3012-3019. (Year: 2000).*

* cited by examiner

ORGANIC ELECTROLUMINESCENT DEVICE COMPRISING A REDOX-DOPED ELECTRON TRANSPORT LAYER AND AN AUXILIARY ELECTRON TRANSPORT LAYER

CROSS REFERENCE TO RELATED APPLICATION

This application claims priority to European Application No. 16195375.7, filed Oct. 24, 2016. The contents of this application is hereby incorporated by reference.

TECHNICAL FIELD

The present invention relates to an organic electroluminescent device, particularly to an organic light emitting diode (OLED) including an ETL stack of at least two electron transport layers, wherein the first electron transport layer comprises a first electron transport matrix compound and the second electron transport layer comprises second electron transport matrix compound and a redox n-dopant, and a device comprising the OLED.

BACKGROUND ART

Organic light-emitting diodes (OLEDs), which are self-emitting devices, have a wide viewing angle, excellent contrast, quick response, high brightness, excellent driving voltage characteristics, and color reproduction. A typical OLED includes an anode, a hole transport layer HTL, an emission layer EML, an electron transport layer ETL, and a cathode, which are sequentially stacked on a substrate. In this regard, the HTL, the EML, and the ETL are thin films formed from organic compounds.

When a voltage is applied to the anode and the cathode, holes injected from the anode move to the EML, via the HTL, and electrons injected from the cathode move to the EML, via the ETL. The holes and electrons recombine in the EML to generate excitons. When the excitons drop from an excited state to a ground state, light is emitted. There is continuing demand for development of improved materials, with the aim that operational voltage is as low as possible while brightness/luminance is high, and that injection and flow of holes and electrons is balanced, so that an OLED having the above-described structure has excellent efficiency and/or a long lifetime.

One of well-established approaches for achieving low operational voltages and high current densities/luminances is electrical p- and/or n-doping in charge injection/charge transport layers, and especially redox doping which generates doped layers with high charge carrier concentrations. In a previous application PCT-KR2015-012551, some of the authors of the present application developed new electron transport matrix compound combining bulky aromatic groups with properly designed electron transport units and successfully proved that an OLED device comprising the inventive electron transport matrix compound in a layer sandwiched between an emitter layer and an electrically doped electron transport layer provides particularly promising results. To enable further increase in device performance, the present invention implements the inventive charge transport compounds in OLEDs comprising redox doped electron transport layer.

DISCLOSURE

Aspects of the present invention provide an organic light-emitting device comprising an emission layer and at least two electron transport layers (ETLs) for increasing the efficiency, such as the external quantum efficiency EQE, low operating voltage and long lifetime, particularly in top and/or bottom emission organic light-emitting diodes (OLEDs).

Another aspect of the present invention provides an electronic device comprising at least one OLED.

According to an aspect of the present invention, there is provided an electroluminescent device comprising an anode, a cathode, an emission layer arranged between the anode and the cathode, a first electron transport layer comprising a first electron transport matrix, a second electron transport layer comprising a second electron transport matrix and a redox n-dopant, wherein the first electron transport layer and the second electron transport layer are arranged between the emission layer and the cathode, wherein the first electron transport layer is arranged closer to the emission layer than the second electron transport layer and the second electron transport layer is arranged closer to the cathode than the first electron transport layer; wherein at least the first electron transport matrix comprises a matrix compound according to formula I:

$$(R^2)_b \quad (R^1)_a$$
$$(R^3)_c \text{—} A^1\text{—}A^2\text{—}A^3\text{—}A^4\text{—}A^5, \quad (I)$$
$$(R^4)_d \quad (R^5)_e$$

wherein
$A^1$, $A^2$, $A^3$ and $A^4$ is independently selected from single bond, an unsubstituted or substituted $C_6$ to $C_{30}$ arylene and an unsubstituted or substituted $C_1$ to $C_{30}$ heteroarylene;

$A^5$ is selected from an unsubstituted or substituted $C_6$ to $C_{40}$ aryl group and/or from an unsubstituted or substituted $C_2$ to $C_{40}$ heteroaryl group;

$R^1$ to $R^5$ are independently a substituted or unsubstituted $C_6$ to $C_{30}$ aryl group, a substituted or unsubstituted $C_2$ to $C_{30}$ heteroaryl group;

a to e are independently an integer of 0 or 1 and $4 \leq a+b+c+d+e \leq 5$; and wherein in the substituted group, at least one hydrogen is replaced by
  (i) deuterium,
  (ii) a halogen,
  (iii) a $C_2$ to $C_{60}$ tertiary amino group, wherein the nitrogen atom of the tertiary amino group is substituted with two independently selected $C_1$ to $C_{30}$ hydrocarbyl groups or the nitrogen atom of the $C_2$ to $C_{60}$ tertiary amino group forms a $C_1$ to $C_{30}$ heterocyclic group,
  (iv) a $C_2$ to $C_{60}$ phosphine oxide group, wherein the phosphorus atom of the phosphine oxide group is substituted with two $C_1$ to $C_{30}$ groups independently selected from hydrocarbyl, halogenated hydrocarbyl and hydrocarbyloxy or the phosphorus atom of the phosphine oxide group forms a $C_1$ to $C_{30}$ heterocyclic group,
  (v) a $C_1$ to $C_{22}$ silyl group,
  (vi) a $C_1$ to $C_{30}$ alkyl group,
  (vii) a $C_1$ to $C_{10}$ alkylsilyl group,
  (viii) a $C_6$ to $C_{22}$ arylsilyl group,
  (ix) a $C_3$ to $C_{30}$ cycloalkyl group,
  (x) a $C_2$ to $C_{30}$ heterocycloalkyl group, (xi) a $C_6$ to $C_{30}$ aryl group,
(xii) a $C_2$ to $C_{30}$ heteroaryl group,
(xiii) a $C_1$ to $C_{20}$ alkoxy group,
(xiv) a $C_1$ to $C_{30}$ perfluoro-hydrocarbyl group,
(xv) a $C_1$ to $C_{10}$ trifluoroalkyl group, or
(xvi) a cyano group.

According to a further embodiment, the first electron transport layer consists of a first matrix compound of formula (I).

Particular aspects of the device are described in detail below.

Operation condition of an electroluminescent device, for example an OLED are described in the experimental part of this specification.

According to a further aspect of the invention the electroluminescent device can be an organic light emitting diode OLED.

In the present specification, "$A^1$, $A^2$, $A^3$ and $A^4$ is independently selected from single bond" means that if "$A^1$, $A^2$, $A^3$ and $A^4$" are selected to be a single bond, "$A^1$, $A^2$, $A^3$ and $A^4$" forms together one single bond.

In the present specification, "$A^1$, $A^2$, $A^3$ and $A^4$ is independently selected from single bond" means that if at least two directly connected members thereof, for example "$A^1$, $A^2$", are selected to be a single bond, these connected members forms together one single bond.

In the present specification, "$A^1$, $A^2$, $A^3$ and $A^4$ is independently selected from single bond" means that if at least three directly connected members thereof, for example "$A^2$, $A^3$, $A^4$", are selected to be a single bond, these directly connected members forms together one single bond.

In the present specification, the term "wherein in the substituted group, at least one hydrogen is replaced by" relates to $A^1$, $A^2$, $A^3$, $A^3$ and $A^5$; to $R^1$ to $R^5$; to $Ar^1$; to L; and to ET; if not otherwise stated.

In the present specification, when a definition is not otherwise provided, "substituted" refers to one substituted with a deuterium, $C_1$ to $C_{12}$ alkyl and $C_1$ to $C_{12}$ alkoxy.

In the present specification, when a definition is not otherwise provided, an "alkyl group" refers to a saturated aliphatic hydrocarbyl group. The alkyl group may be a $C_1$ to $C_{12}$ alkyl group. More specifically, the alkyl group may be a $C_1$ to $C_{10}$ alkyl group or a $C_1$ to $C_6$ alkyl group. For example, a $C_1$ to $C_4$ alkyl group includes 1 to 4 carbons in alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group.

The term "cycloalkyl" refers to saturated hydrocarbyl groups derived from a cycloalkane by formal abstraction of one hydrogen atom from a ring atom comprised in the corresponding cycloalkane. Examples of the cycloalkyl group may be a cyclopropyl group, a cyclobutyl group, a cyclopentyl group, a cyclohexyl group, a methylcyclohexyl group, an adamantly group and the like.

In the present specification, "aryl group" refers to a hydrocarbyl group which can be created by formal abstraction of one hydrogen atom from an aromatic ring in the corresponding aromatic hydrocarbon. Aromatic hydrocarbon refers to a hydrocarbon which contains at least one aromatic ring or aromatic ring system. Aromatic ring or aromatic ring system refers to a planar ring or ring system of covalently bound carbon atoms, wherein the planar ring or ring system comprises a conjugated system of delocalized electrons fulfilling Hückel's rule. Examples of aryl groups include monocyclic groups like phenyl or tolyl, polycyclic groups which comprise more aromatic rings linked by single bonds, like biphenylyl, and polycyclic groups comprising fused rings, like naphtyl or fluoren-2-yl.

Analogously, under heteroaryl, it is understood a group derived by formal abstraction of one ring hydrogen from a heterocyclic aromatic ring in a compound comprising at least one such ring.

Under heterocycloalkyl, it is understood a group derived by formal abstraction of one ring hydrogen from a saturated heterocyclic ring in a compound comprising at least one such ring.

The term "hetero" is understood the way that at least one carbon atom, in a structure which may be formed by covalently bound carbon atoms, is replaced by another polyvalent atom. Preferably, the heteroatoms are selected from B, Si, N, P, O, S; more preferably from N, P, O, S.

In the present specification, the single bond refers to a direct bond.

In the context of the present invention, "different" means that the compounds do not have an identical chemical structure.

The term "free of", "does not contain", "does not comprise" does not exclude impurities which may be present in the compounds prior to deposition. Impurities have no technical effect with respect to the object achieved by the present invention.

The term "contacting sandwiched" refers to an arrangement of three layers whereby the layer in the middle is in direct contact with the two adjacent layers.

In the specification, hole characteristics refer to an ability to donate an electron to form a hole when an electric field is applied and that a hole formed in the anode may be easily injected into the emission layer and transported in the emission layer due to conductive characteristics according to a highest occupied molecular orbital (HOMO) level.

In addition, electron characteristics refer to an ability to accept an electron when an electric field is applied and that electron formed in the cathode may be easily injected into the emission layer and transported in the emission layer due to conductive characteristics according to a lowest unoccupied molecular orbital (LUMO) level.

Advantageous Effects

Surprisingly, it was found that the organic light emitting device of the invention solves the problem underlying the present invention by being in various aspects superior over the organic electroluminescent devices known in the art, in particular with respect to voltage and/or efficiency. These parameters are important for high efficiency and thereby increased battery life of a mobile device, for example a mobile display device.

The inventors have surprisingly found that particularly good performance can be achieved when using the organic electroluminescent device as a fluorescent blue device.

The specific arrangements mentioned herein as preferred were found to be particularly advantageous.

Further an organic electroluminescent device having high efficiency and/or long life-span may be realized.

Hereinafter, an ETL layer stack comprising a first and second electron transport layer according to an embodiment is described.

First Electron Transport Matrix Compound

Similar as other compounds comprised in the inventive device outside the emitting layer, the first electron transport matrix compound may not emit light under the operation condition of an electroluminescent device, for example an OLED.

According to a further embodiment, the first matrix compound is a compound according to formula (Ia):

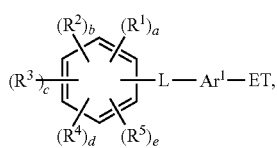

(Ia)

wherein, in formula Ia,
$Ar^1$ is selected from $C_6$ to $C_{12}$ arylene and $C_1$ to $C_{11}$ heteroarylene;
$R^1$ to $R^5$ are independently a substituted or unsubstituted C6 to C30 aryl group, a substituted or unsubstituted $C_2$ to $C_{30}$ heteroaryl group;
a to e are independently an integer of 0 or 1 and $4 \leq a+b+c+d+e \leq 5$;
L is a single bond, a substituted or unsubstituted $C_6$ to $C_{30}$ arylene group, or a substituted or unsubstituted $C_2$ to $C_{30}$ heteroarylene group;
ET is a unsubstituted $C_6$ to $C_{40}$ aryl or a unsubstituted $C_5$ to $C_{40}$ heteroaryl group, or a substituted $C_6$ to $C_{40}$ aryl or a substituted $C_5$ to $C_{40}$ heteroaryl group; and
wherein in the substituted group, at least one hydrogen is replaced by
  (i) deuterium,
  (ii) a halogen,
  (iii) a $C_2$ to $C_{60}$ tertiary amino group, wherein the nitrogen atom of the $C_2$ to $C_{60}$ tertiary amino group is substituted with two independently selected $C_1$ to $C_{30}$ hydrocarbyl groups or forms a $C_1$ to $C_{30}$ heterocyclic group,
  (iv) a $C_2$ to $C_{60}$ phosphine oxide group, wherein the phosphorus atom of the phosphine oxide group is substituted with two $C_1$ to $C_{30}$ groups independently selected from hydrocarbyl, halogenated hydrocarbyl and hydrocarbyloxy or the phosphorus atom of the phosphine oxide group forms a $C_1$ to $C_{30}$ heterocyclic group,
  (v) a $C_1$ to $C_{22}$ silyl group,
  (vi) a $C_1$ to $C_{30}$ alkyl group,
  (vii) a $C_1$ to $C_{10}$ alkylsilyl group,
  (viii) a $C_6$ to $C_{22}$ arylsilyl group,
  (ix) a $C_3$ to $C_{30}$ cycloalkyl group,
  (x) a $C_2$ to $C_{30}$ heterocycloalkyl group,
  (xi) a $C_6$ to $C_{30}$ aryl group,
  (xii) a $C_2$ to $C_{30}$ heteroaryl group,
  (xiii) a $C_1$ to $C_{20}$ alkoxy group,
  (xiv) a $C_1$ to $C_{30}$ perfluoro-hydrocarbyl group,
  (xv) a $C_1$ to $C_{10}$ trifluoroalkyl group, or
  (xvi) a cyano group.

In one embodiment, the ET group is not a carbazolyl group.

According to a further embodiment, in formula (Ia):
$R^1$ to $R^5$ are independently a substituted or unsubstituted $C_6$ to $C_{12}$ aryl group, a substituted or unsubstituted $C_5$ to $C_9$ heteroaryl group;
a to e are independently an integer of 0 or 1 and $4 \leq a+b+c+d+e \leq 5$;
L is a single bond, a substituted or unsubstituted $C_6$ to $C_{12}$ arylene group, or a substituted or unsubstituted $C_5$ to $C_9$ heteroarylene group;
ET is a unsubstituted $C_6$ to $C_{18}$ aryl or a unsubstituted $C_5$ to $C_{20}$ heteroaryl group or a substituted $C_6$ to $C_{18}$ aryl or a substituted $C_6$ to $C_{20}$ heteroaryl group; and
wherein in the substituted group, at least one hydrogen is replaced by
  (i) deuterium,
  (ii) a $C_1$ to $C_{12}$ alkyl group,
  (iii) a $C_6$ to $C_{12}$ aryl group,
  (iv) a $C_5$ to $C_9$ heteroaryl group, or
  (v) a $C_1$ to $C_{12}$ alkoxy group.

In one embodiment, the ET group is not a carbazolyl group.

According to a further embodiment, $Ar^1$ is phenyl or biphenylyl and L is a single bond. According to a further embodiment, the first electron transport compound is a compound according to formula (Ib):

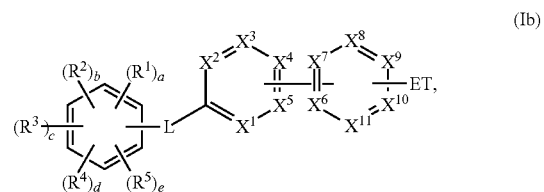

(Ib)

wherein in formula Ib:
$X^1$ to $X^{11}$ are independently, N, C, or $CR^a$;
$R^a$ is independently, hydrogen, deuterium, a $C_1$ to $C_{30}$ alkyl group, a $C_3$ to $C_{30}$ cycloalkyl group, a $C_6$ to $C_{30}$ aryl group, a $C_6$ to $C_{30}$ diarylamine group, a $C_1$ to $C_{30}$ alkoxy group, a $C_3$ to $C_{21}$ silyl group, a $C_3$ to $C_{21}$ silyloxy group, a $C_1$ to $C_{30}$ alkylthio group, a $C_6$ to $C_{30}$ arylthio group, a halogen, a $C_1$ to $C_{30}$ halogenated hydrocarbyl group, a cyano group;
$R^1$ to $R^5$ are independently a substituted or unsubstituted $C_6$ to $C_{30}$ aryl group, a substituted or unsubstituted $C_2$ to $C_{30}$ heteroaryl group;
a to e are independently an integer of 0 or 1 and $4 \leq a+b+c+d+e \leq 5$;
L is a single bond, a substituted or unsubstituted $C_6$ to $C_{30}$ arylene group, a substituted or unsubstituted $C_2$ to $C_{30}$ heteroarylene group;
ET is a unsubstituted $C_6$ to $C_{40}$ aryl or a unsubstituted $C_2$ to $C_{40}$ heteroaryl group, or a substituted $C_6$ to $C_{40}$ aryl or a substituted $C_2$ to $C_{40}$ heteroaryl group; and
wherein in the substituted group, at least one hydrogen is replaced by
  (i) deuterium,
  (ii) a halogen,
  (iii) a $C_1$ to $C_{60}$ tertiary amino group, wherein the nitrogen atom of the $C_2$ to $C_{60}$ tertiary amino group is substituted with two independently selected $C_1$ to $C_{30}$ hydrocarbyl groups or forms a $C_1$ to $C_{30}$ heterocyclic group,
  (iv) a $C_2$ to $C_{60}$ phosphine oxide group, wherein the phosphorus atom of the phosphine oxide group is substituted with two $C_1$ to $C_{30}$ groups independently selected from hydrocarbyl, halogenated hydrocarbyl and hydrocarbyloxy or the phosphorus atom of the phosphine oxide group forms a $C_1$ to $C_{30}$ heterocyclic group,
  (v) a $C_1$ to $C_{22}$ silyl group,
  (vi) a $C_1$ to $C_{30}$ alkyl group,
  (vii) a $C_1$ to $C_{10}$ alkylsilyl group,
  (viii) a $C_6$ to $C_{22}$ arylsilyl group,
  (ix) a $C_3$ to $C_{30}$ cycloalkyl group, (x) a $C_2$ to $C_{30}$ heterocycloalkyl group,
(xi) a $C_6$ to $C_{30}$ aryl group,
(xii) a $C_2$ to $C_{30}$ heteroaryl group,
(xiii) a $C_1$ to $C_{20}$ alkoxy group,
(xiv) a $C_1$ to $C_{30}$ perfluoro-hydrocarbyl group,
(xv) a $C_1$ to $C_{10}$ trifluoroalkyl group, or
(xvi) a cyano group.

Preferably, $R^a$ is independently selected from hydrogen, deuterium, a $C_1$ to $C_{30}$ alkyl group, a $C_3$ to $C_{30}$ cycloalkyl group, a $C_6$ to $C_{30}$ aryl group, or a $C_1$ to $C_{30}$ alkoxy group.

In one embodiment, the ET group is not a carbazolyl group.

According to a further embodiment, a first electron transport layer comprises a first electron matrix compound according to formula (Ic)

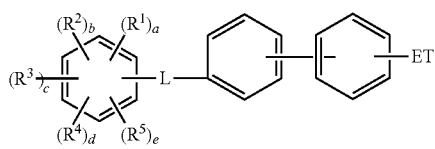

wherein in formula Ic:
$R^1$ to $R^5$ are independently a substituted or unsubstituted $C_6$ to $C_{30}$ aryl group, a substituted or unsubstituted $C_2$ to $C_{30}$ heteroaryl group;
a to e are independently an integer of 0 or 1 and $4 \leq a+b+c+d+e \leq 5$,
L is a single bond, a substituted or unsubstituted $C_6$ to $C_{30}$ arylene group, a substituted or unsubstituted $C_2$ to $C_{30}$ heteroarylene group, and
ET is a unsubstituted $C_6$ to $C_{40}$ aryl or a unsubstituted $C_2$ to $C_{40}$ heteroaryl group, or a substituted $C_6$ to $C_{40}$ aryl or a substituted $C_2$ to $C_{40}$ heteroaryl group; and
wherein in the substituted group, at least one hydrogen is replaced by
  (i) deuterium,
  (ii) a halogen,
  (iii) a $C_1$ to $C_{60}$ tertiary amino group, wherein the nitrogen atom of the $C_2$ to $C_{60}$ tertiary amino group is substituted with two independently selected $C_1$ to $C_{30}$ hydrocarbyl groups or forms a $C_1$ to $C_{30}$ heterocyclic group,
  (iv) a $C_2$ to $C_{60}$ phosphine oxide group, wherein the phosphorus atom of the phosphine oxide group is substituted with two $C_1$ to $C_{30}$ groups independently selected from hydrocarbyl, halogenated hydrocarbyl and hydrocarbyloxy or the phosphorus atom of the phosphine oxide group forms a $C_1$ to $C_{30}$ heterocyclic group
  (v) a $C_1$ to $C_{22}$ silyl group,
  (vi) a $C_1$ to $C_{30}$ alkyl group,
  (vii) a $C_1$ to $C_{10}$ alkylsilyl group,
  (viii) a $C_6$ to $C_{22}$ arylsilyl group,
  (ix) a $C_3$ to $C_{30}$ cycloalkyl group,
  (x) a $C_2$ to $C_{30}$ heterocycloalkyl group,
  (xi) a $C_6$ to $C_{30}$ aryl group,
  (xii) a $C_2$ to $C_{30}$ heteroaryl group,
  (xiii) a $C_1$ to $C_{20}$ alkoxy group,
  (xiv) a $C_1$ to $C_{30}$ perfluoro-hydrocarbyl group,
  (xv) a $C_1$ to $C_{10}$ trifluoroalkyl group, or
  (xvi) a cyano group.

In one embodiment, the ET group is not a carbazolyl group.

According to a further embodiment, in formula (Ic):

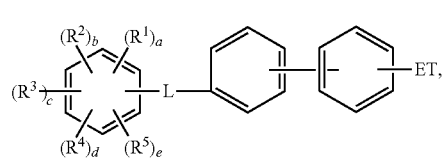

$R^1$ to $R^5$ are independently a substituted or unsubstituted $C_6$ to $C_{30}$ aryl group, a substituted or unsubstituted $C_2$ to $C_{30}$ heteroaryl group;
a to d are 1;
e is 0;
L is a single bond, a substituted or unsubstituted $C_6$ to $C_{30}$ arylene group, a substituted or unsubstituted $C_2$ to $C_{30}$ heteroarylene group,
ET is a unsubstituted $C_6$ to $C_{40}$ aryl or a unsubstituted $C_2$ to $C_{40}$ heteroaryl group, or a substituted $C_6$ to $C_{40}$ aryl or a substituted $C_2$ to $C_{40}$ heteroaryl group; and
wherein in the substituted group, at least one hydrogen is replaced by
  (i) deuterium,
  (ii) a halogen,
  (iii) a $C_1$ to $C_{60}$ tertiary amino group, wherein the nitrogen atom of the $C_2$ to $C_{60}$ tertiary amino group is substituted with two independently selected $C_1$ to $C_{30}$ hydrocarbyl groups or forms a $C_1$ to $C_{30}$ heterocyclic group,
  (iv) a $C_1$ to $C_{22}$ silyl group,
  (v) a $C_1$ to $C_{30}$ alkyl group,
  (vi) a $C_1$ to $C_{10}$ alkylsilyl group,
  (vii) a $C_6$ to $C_{22}$ arylsilyl group,
  (viii) a $C_3$ to $C_{30}$ cycloalkyl group,
  (ix) a $C_2$ to $C_{30}$ heterocycloalkyl group,
  (x) a $C_6$ to $C_{30}$ aryl group,
  (xi) a $C_2$ to $C_{30}$ heteroaryl group,
  (xii) a $C_1$ to $C_{20}$ alkoxy group,
  (xiii) a $C_1$ to $C_{30}$ perfluoro-hydrocarbyl group,
  (xiv) a $C_1$ to $C_{10}$ trifluoroalkyl group, or
  (xv) a cyano group.

Preferably, $R^1$ to $R^5$ are independently selected from a substituted or unsubstituted $C_6$ to $C_{18}$ aryl group or $C_5$ to $C_{18}$ heteroaryl group, more preferred from a substituted or unsubstituted $C_6$ to $C_{18}$ aryl group. Preferably, $R^1$ to $R^5$ are unsubstituted. In one embodiment, the ET group is not a carbazolyl group.

Particularly good performance can be achieved when the compound of formula I is selected in this range, in particular in layers which are deposited in vacuum.

One or more substituents may be selected from $C_4$ to $C_{12}$ alkyl or $C_4$ to $C_{12}$ alkoxy.

Particularly good properties in solution processed layers may be obtained, when the compound of formula I is selected in this range.

Preferably, L is selected from a single bond or unsubstituted phenyl.

According to a further embodiment, the ET group is a $C_2$ to $C_{30}$ heteroaryl group, preferably ET is selected from formula E1 or E2:

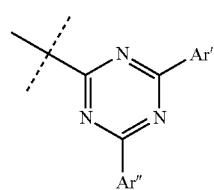

and

-continued

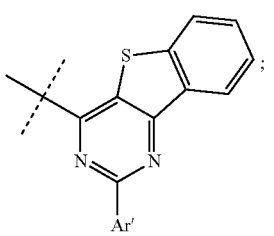
E2 wherein

Ar' and Ar" are independently selected from $C_6$ to $C_{18}$ aryl, preferably from $C_6$ to $C_{12}$ aryl.

Preferably, ET is selected from formula E1.

Preferably, the compound of formula I is essentially non-emissive.

In the context of the present specification the term "essentially non-emissive" means that the contribution of the compound or layer to the visible emission spectrum from the device is less than 10%, preferably less than 5% relative to the visible emission spectrum. The visible emission spectrum is an emission spectrum with a wavelength of about ≥380 nm to about ≤780 nm.

According to a further aspect of the invention, the reduction potential of the first electron transport matrix compound, if measured under the same conditions by cyclic voltammetry against Fc/Fc$^+$ in tetrahydrofuran, may have a value which is less negative than the value obtained for triphenylphosphine oxide and more negative than the value obtained for tetrakis(quinoxalin-5-yloxy)zirconium.

Under these conditions the reduction potential of triphenylphosphine oxide is about −3.06 V and the reduction potential of tetrakis(quinoxalin-5-yloxy)zirconium is about −1.78 V.

According to a further aspect of the invention, the reduction potential of the first electron transport matrix compound, if measured under the same conditions by cyclic voltammetry against Fc/Fc$^+$ in tetrahydrofuran, may have a value which is less negative than the respective value obtained for triphenylphosphine oxide, preferably less negative than the respective value for bis(4-(9H-carbazol-9-yl)phenyl)-(phenyl)phosphine oxide, more preferably less negative than the respective value for 3-([1,1'-biphenyl]-4-yl)-5-(4-(tert-butyl)phenyl)-4-phenyl-4H-1,2,4-triazole, even more preferably less negative than the respective value for pyrene, most preferably less negative than the respective value for 2,7-di-pyrenyl-9,9-spirobifluorene, also preferably less negative than the respective value for 4,7-diphenyl-1,10-phenanthroline, also preferably less negative than the respective value for 2,4,7,9-tetraphenyl-1,10-phenanthroline, also preferably less negative than the respective value for 7-([1,1'-biphenyl]-4-yl)dibenzo[c,h]acridine, also preferably less negative than the respective value for 2,4,6-triphenyltriazine, and still preferably less negative than the respective value for 2,4,6-tri(biphenyl-4-yl)-1,3,5-triazine.

According to a further aspect of the invention, the reduction potential of the first electron transport matrix compound, if measured under the same conditions by cyclic voltammetry against Fc/Fc$^+$ in tetrahydrofuran, may have the value which is more negative than the respective value obtained for tetrakis(quinoxalin-5-yloxy)zirconium, preferably more negative than the respective value for 4,4'-bis(4,6-diphenyl-1,3,5-triazin-2-yl)-1,1'-biphenyl, most preferably more negative than the respective value for 2,4,6-tri(biphenyl-4-yl)-1,3,5-triazine.

According to a further aspect of the invention, the reduction potential of the first electron matrix compound may be selected less negative than −2.35 V and more negative than −2.14 V, preferably less negative than −2.3 V and more negative than −2.16 V, more preferably less negative than −2.25 V and more negative than −2.16 V, when measured against Fc/Fc$^+$ in tetrahydrofuran.

The reduction potential can be determined by cyclic voltammetry with potentiostatic device Metrohm PGSTAT30 and software Metrohm Autolab GPES at room temperature. The reduction potentials given at particular compounds were measured in an argon de-aerated, dry 0.1M THF solution of the tested substance, under argon atmosphere, with 0.1M tetrabutylammonium hexafluorophosphate supporting electrolyte, between platinum working electrodes and with an Ag/AgCl pseudo-standard electrode (Metrohm Silver rod electrode), consisting of a silver wire covered by silver chloride and immersed directly in the measured solution, with the scan rate 100 mV/s. The first run was done in the broadest range of the potential set on the working electrodes, and the range was then adjusted within subsequent runs appropriately. The final three runs were done with the addition of ferrocene (in 0.1M concentration) as the standard. The average of potentials corresponding to cathodic and anodic peak of the studied compound, after subtraction of the average of cathodic and anodic potentials observed for the standard Fc$^+$/Fc redox couple, afforded finally the values reported above. All studied compounds as well as the reported comparative compounds showed well-defined reversible electrochemical behaviour.

According to another aspect, the compound of formula I may have a glass transition temperature (Tg) selected between ≥125° C. and ≤200° C., preferably ≥130° C. and ≤180° C.

The glass transition temperature can be measured under nitrogen and using a heating rate of 10 K per min in a Mettler Toledo DSC 822e differential scanning calorimeter as described in DIN EN ISO 11357, published in March 2010.

Particularly preferred may be compounds of formula I with the following structures A1 to A18:

A1
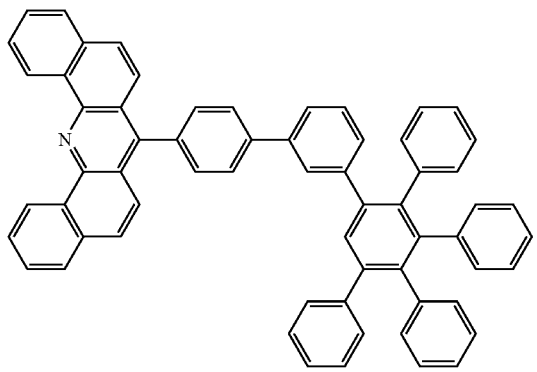
A2
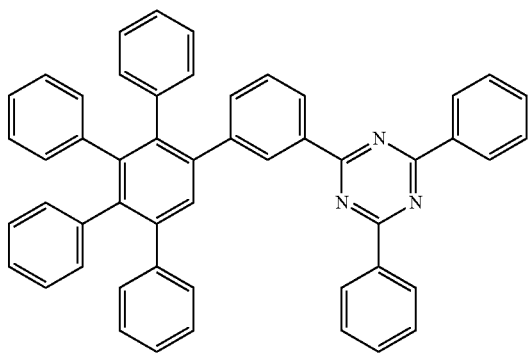 [SMILES: c1ccc(-c2nc(-c3ccccc3)nc(-c3cccc(-c4cc(-c5ccccc5)c(-c5ccccc5)c(-c5ccccc5)c4-c4ccccc4)c3)n2)cc1]
A3
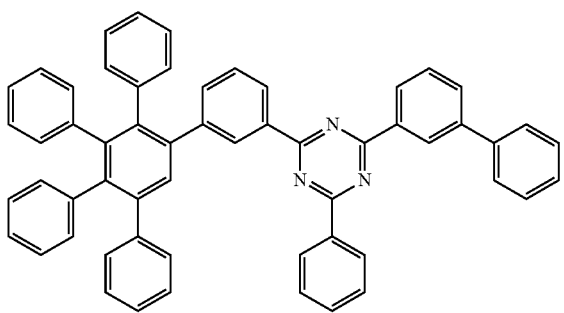 [SMILES: c1ccc(-c2cccc(-c3nc(-c4ccccc4)nc(-c4cccc(-c5cc(-c6ccccc6)c(-c6ccccc6)c(-c6ccccc6)c5-c5ccccc5)c4)n3)c2)cc1]
A4
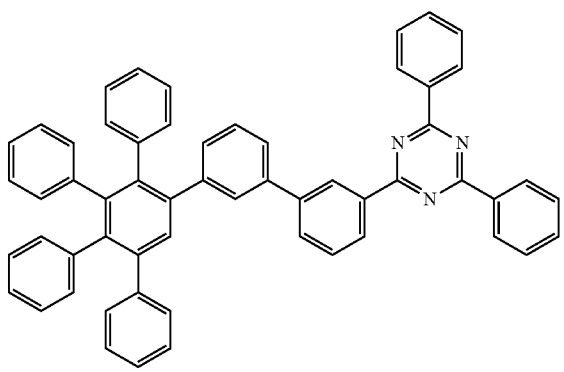 [SMILES: c1ccc(-c2nc(-c3ccccc3)nc(-c3cccc(-c4cccc(-c5cc(-c6ccccc6)c(-c6ccccc6)c(-c6ccccc6)c5-c5ccccc5)c4)c3)n2)cc1]
A5
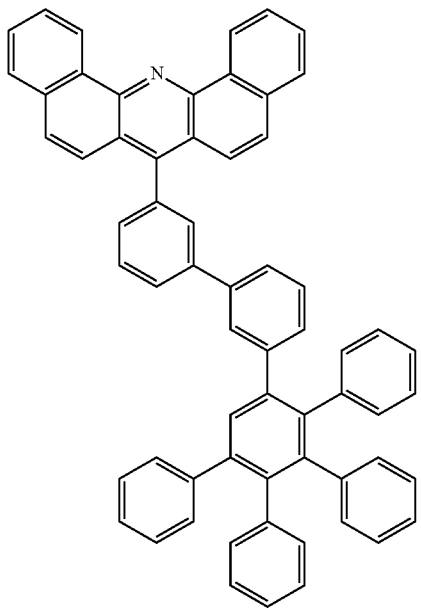 [SMILES: c1ccc(-c2cc(-c3cccc(-c4cccc(-c5c6ccc7ccccc7c6nc6c5ccc5ccccc56)c4)c3)c(-c3ccccc3)c(-c3ccccc3)c2-c2ccccc2)cc1]
A6
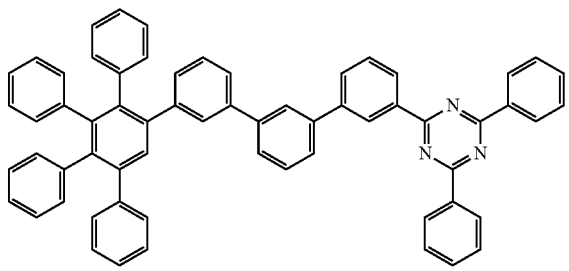 [SMILES: c1ccc(-c2nc(-c3ccccc3)nc(-c3cccc(-c4cccc(-c5cccc(-c6cc(-c7ccccc7)c(-c7ccccc7)c(-c7ccccc7)c6-c6ccccc6)c5)c4)c3)n2)cc1]

-continued
A7
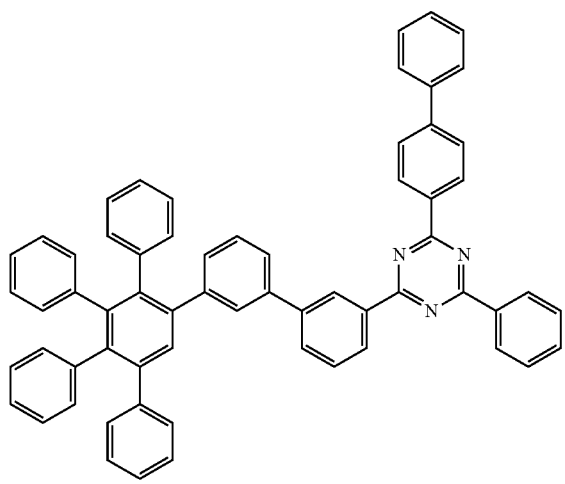 [SMILES: c1ccc(-c2ccc(-c3nc(-c4ccccc4)nc(-c4cccc(-c5cccc(-c6cc(-c7ccccc7)c(-c7ccccc7)c(-c7ccccc7)c6-c6ccccc6)c5)c4)n3)cc2)cc1]
A8
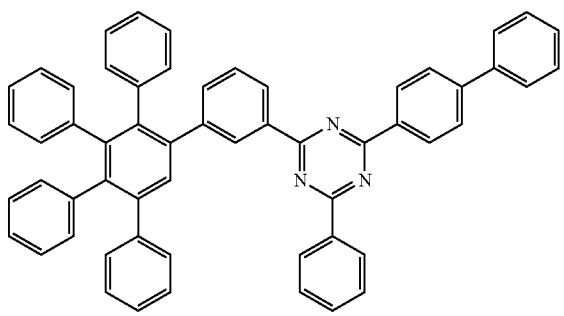 [SMILES: c1ccc(-c2ccc(-c3nc(-c4ccccc4)nc(-c4cccc(-c5cc(-c6ccccc6)c(-c6ccccc6)c(-c6ccccc6)c5-c5ccccc5)c4)n3)cc2)cc1]
A9
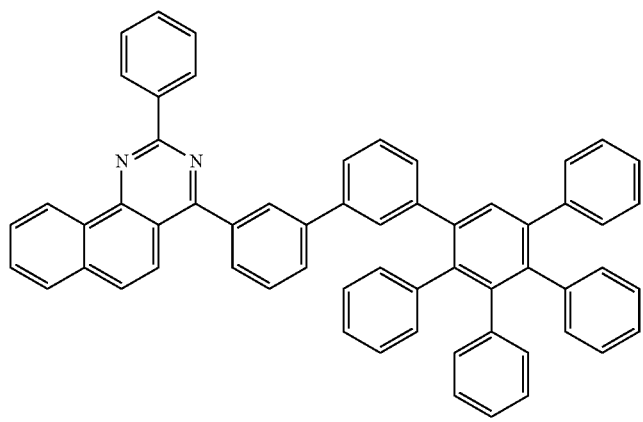 [SMILES: c1ccc(-c2nc(-c3cccc(-c4cccc(-c5cc(-c6ccccc6)c(-c6ccccc6)c(-c6ccccc6)c5-c5ccccc5)c4)c3)c3ccc4ccccc4c3n2)cc1]
A10
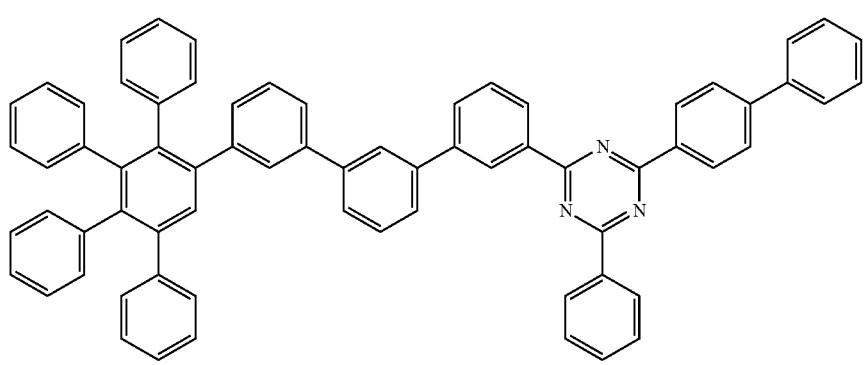 [SMILES: c1ccc(-c2ccc(-c3nc(-c4ccccc4)nc(-c4cccc(-c5cccc(-c6cccc(-c7cc(-c8ccccc8)c(-c8ccccc8)c(-c8ccccc8)c7-c7ccccc7)c6)c5)c4)n3)cc2)cc1]
A11
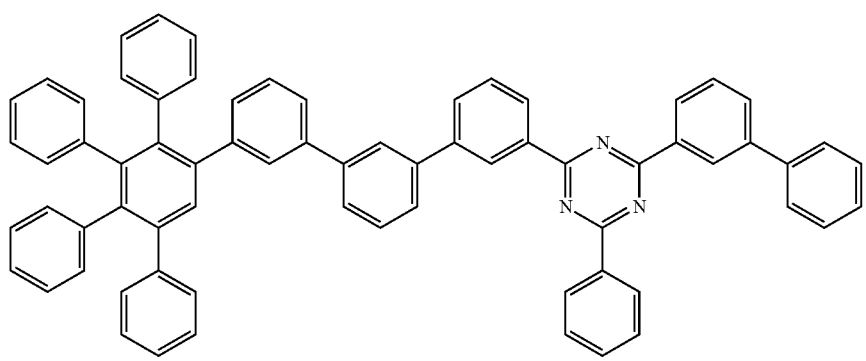

-continued
A12
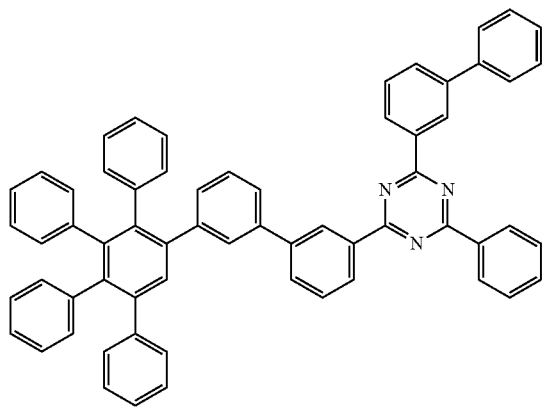 [SMILES: c1ccc(-c2cccc(-c3nc(-c4ccccc4)nc(-c4cccc(-c5cccc(-c6cc(-c7ccccc7)c(-c7ccccc7)c(-c7ccccc7)c6-c6ccccc6)c5)c4)n3)c2)cc1]
A13
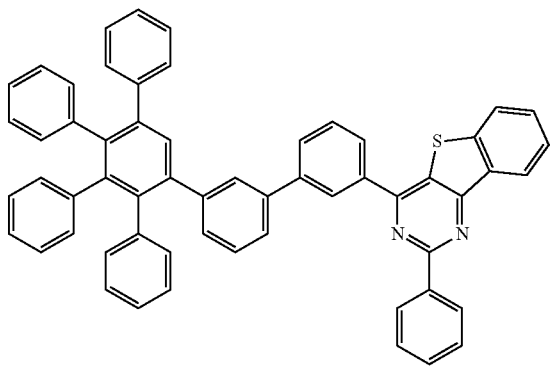 [SMILES: c1ccc(-c2nc(-c3cccc(-c4cccc(-c5cc(-c6ccccc6)c(-c6ccccc6)c(-c6ccccc6)c5-c5ccccc5)c4)c3)c3sc4ccccc4c3n2)cc1]
A14
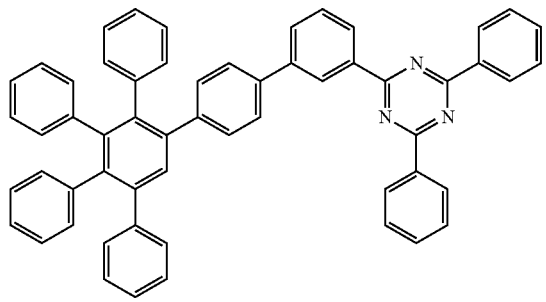
A15
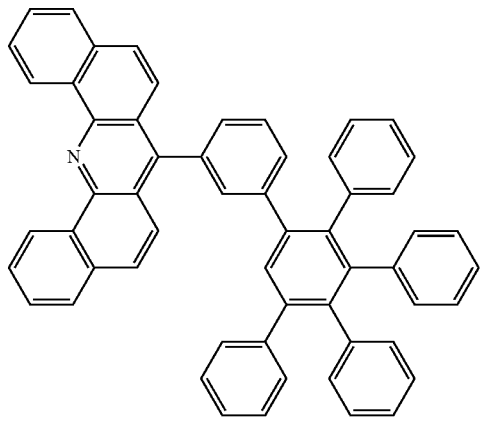
A16
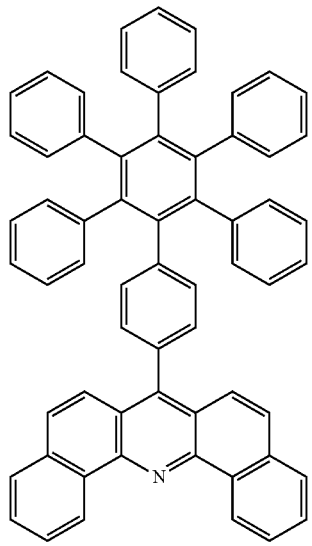 [SMILES: c1ccc(-c2c(-c3ccccc3)c(-c3ccccc3)c(-c3ccc(-c4c5ccc6ccccc6c5nc5c4ccc4ccccc45)cc3)c(-c3ccccc3)c2-c2ccccc2)cc1]
A17
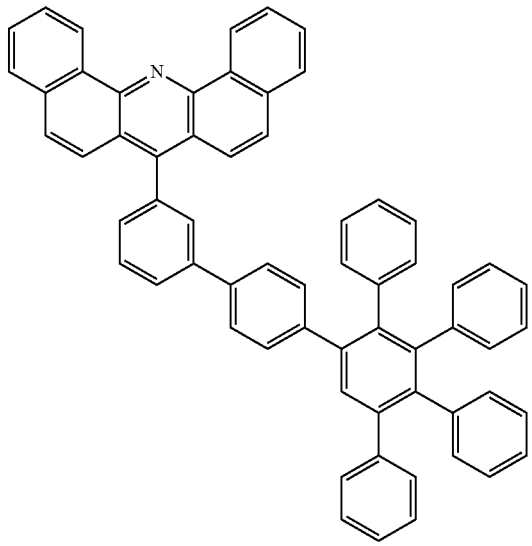

A18

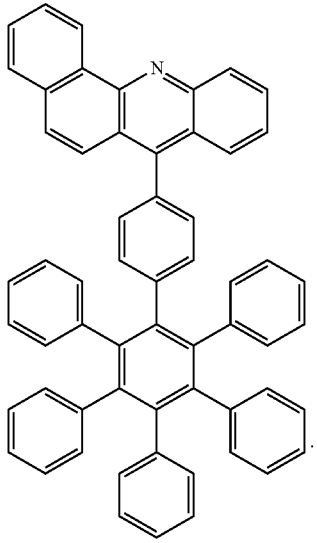

Second Electron Transport Matrix Compound

Second electron transport matrix is not particularly limited. Similarly as other materials which are in the inventive device comprised outside the emitting layer, the second electron transport matrix may not emit light.

According to one embodiment, the second electron transport matrix can be an organic compound, an organometallic compound, or a metal complex.

According to one embodiment, the second electron transport matrix may be a covalent compound comprising a conjugated system of at least 6 delocalized electrons. Under a covalent material in a broadest possible sense, it might be understood a material, wherein at least 50% of all chemical bonds are covalent bonds, wherein coordination bonds are also considered as covalent bonds. In the present application, the term encompasses in the broadest sense all usual electron transport matrices which are predominantly selected from organic compounds but also e.g. from compounds comprising structural moieties which do not comprise carbon, for example substituted 2,4,6-tribora-1,3,5 triazines, or from metal complexes, for example aluminium tris(8-hydroxyquinolinolate).

The molecular covalent materials can comprise low molecular weight compounds which may be, preferably, stable enough to be processable by vacuum thermal evaporation (VTE). Alternatively, covalent materials can comprise polymeric covalent compounds, preferably, compounds soluble in a solvent and thus processable in form of a solution. It is to be understood that a polymeric substantially covalent material may be crosslinked to form an infinite irregular network, however, it is supposed that such crosslinked polymeric substantially covalent matrix compound still comprises both skeletal as well as peripheral atoms. Skeletal atoms of the covalent compound are covalently bound to at least two neighbour atoms. Other atoms of the covalent compound are peripheral atoms which are covalently bound with a single neighbour atom. Inorganic infinite crystals or fully crosslinked networks having partly covalent bonding but substantially lacking peripheral atoms, like silicon, germanium, gallium arsenide, indium phosphide, zinc sulfide, silicate glass etc are not considered as covalent matrices in the sense of present application, because such fully crosslinked covalent materials comprise peripheral atoms only on the surface of the phase formed by such material. A compound comprising cations and anions is still considered as covalent, if at least the cation or at least the anion comprises at least ten covalently bound atoms.

Preferred examples of covalent second electron transport matrix compounds are organic compounds, consisting predominantly from covalently bound C, H, O, N, S, which may optionally comprise also covalently bound B, P, As, Se. In one embodiment, the second electron transport matrix compound lacks metal atoms and majority of its skeletal atoms is selected from C, O, S, N.

In another embodiment, the second electron transport matrix compound comprises a conjugated system of at least six, more preferably at least ten, even more preferably at least fourteen delocalized electrons.

Examples of conjugated systems of delocalized electrons are systems of alternating pi- and sigma bonds. Optionally, one or more two-atom structural units having the pi-bond between its atoms can be replaced by an atom bearing at least one lone electron pair, typically by a divalent atom selected from O, S, Se, Te or by a trivalent atom selected from N, P, As, Sb, Bi. Preferably, the conjugated system of delocalized electrons comprises at least one aromatic or heteroaromatic ring adhering to the Hückel rule. Also preferably, the second electron transport matrix compound may comprise at least two aromatic or heteroaromatic rings which are either linked by a covalent bond or condensed.

In one of specific embodiments, the second electron transport matrix compound comprises a ring consisting of covalently bound atoms and at least one atom in the ring is phosphorus.

In a more preferred embodiment, the phosphorus-containing ring consisting of covalently bound atoms is a phosphepine ring.

In another preferred embodiment, the covalent matrix compound comprises a phosphine oxide group. Also preferably, the substantially covalent matrix compound comprises a heterocyclic ring comprising at least one nitrogen atom. Examples of nitrogen containing heterocyclic compounds which are particularly advantageous as second electron transport matrix compound for the inventive device are matrices comprising, alone or in combination, pyridine structural moieties, diazine structural moieties, triazine structural moieties, quinoline structural moieties, benzoquinoline structural moieties, quinazoline structural moieties, acridine structural moieties, benzacridine structural moieties, dibenzacridine structural moieties, diazole structural moieties and benzodiazole structural moieties.

The second matrix compound may have a molecular weight (Mw) of ≥400 to ≤850 g/mol, preferably ≥450 to ≤830 g/mol. If the molecular weight is selected in this range, particularly reproducible evaporation and deposition can be achieved in vacuum at temperatures where good long-term stability is observed.

Preferably, the second electron transport matrix compound may be essentially non-emissive.

In one embodiment, the dipole moment of the compound of the second electron transport matrix compound may be selected ≥0 and ≤2.3 Debye, preferably ≥0.8 and ≤2.2 Debye, also preferred ≥1 and ≤2.2 Debye, also preferred ≥1.5 and ≤2.2 Debye. In another embodiment, the second electron transport matrix compound may have dipole moment higher than 2.3 Debye. It may be a preferred embodiment in combination with redox dopants selected from elemental metals.

According to another aspect, the reduction potential of the second electron transport matrix compound may be selected more negative than −2.2 V and less negative than −2.35 V against Fc/Fc$^+$ in tetrahydrofuran, preferably more negative than −2.25 V and less negative than −2.3 V.

Redox n-Dopant

Under redox n-dopant, it is understood a compound which, if embedded into an electron transport matrix, increases concentration of free electrons in comparison with the neat matrix under the same physical conditions.

The redox n-dopant may not emit light under the operation condition of an electroluminescent device, for example an OLED. In one embodiment, the redox n-dopant is selected from an elemental metal, an electrically neutral metal complex and/or an electrically neutral organic radical.

The most practical benchmark for the strength of an n-dopant is the value of its redox potential. There is no particular limitation in terms how negative the value of the redox potential can be. As reduction potentials of usual electron transport matrices used in organic light emitting diodes are, if measured by cyclic voltammetry against ferrocene/ferrocenium reference redox couple, roughly in the range from about −1.8 V to about −3.1V; the practically applicable range of redox potentials for n-dopants which can effectively n-dope such matrices is in a slightly broader range, from about −1.7 V to about −3.3 V.

The measurement of redox potentials is practically performed for a corresponding redox couple consisting of the reduced and of the oxidized form of the same compound.

In case that the redox n-dopant is an electrically neutral metal complex and/or an electrically neutral organic radical, the measurement of its redox potential is actually performed for the redox couple formed by
  (i) the electrically neutral metal complex and its cation radical formed by an abstraction of one electron from the electrically neutral metal complex, or
  (ii) the electrically neutral organic radical and its cation formed by an abstraction of one electron from the electrically neutral organic radical.

Preferably, the redox potential of the electrically neutral metal complex and/or of the electrically neutral organic radical may have a value which is more negative than −1.7 V, preferably more negative than −1.9 V, more preferably more negative than −2.1 V, even more preferably more negative than −2.3 V, most preferably more negative than −2.5 V, if measured by cyclic voltammetry against ferrocene/ferrocenium reference redox couple for a corresponding redox couple consisting of
  (i) the electrically neutral metal complex and its cation radical formed by an abstraction of one electron from the electrically neutral metal complex, or
  (ii) the electrically neutral organic radical and its cation formed by an abstraction of one electron from the electrically neutral organic radical.

In a preferred embodiment, the redox potential of the n-dopant is between the value which is about 0.5 V more positive and the value which is about 0.5 V more negative than the value of the reduction potential of the chosen electron transport matrix.

Electrically neutral metal complexes suitable as redox n-dopants may be e.g. strongly reductive complexes of some transition metals in low oxidation state. Particularly strong redox n-dopants may be selected for example from Cr(II), Mo(II) and/or W(II) guanidinate complexes such as $W_2(hpp)_4$, as described in more detail in WO2005/086251.

Electrically neutral organic radicals suitable as redox n-dopants may be e.g. organic radicals created by supply of additional energy from their stable dimers, oligomers or polymers, as described in more detail in EP 1 837 926 B1, WO2007/107306, or WO2007/107356.

Under an elemental metal, it is understood a metal in a state of a neat metal, of a metal alloy, or in a state of free atoms or metal clusters. It is understood that metals deposited by vacuum thermal evaporation from a metallic phase, e.g. from a neat bulk metal, vaporize in their elemental form. It is further understood that if the vaporized elemental metal is deposited together with a covalent matrix, the metal atoms and/or clusters are embedded in the covalent matrix. In other words, it is understood that any metal doped covalent material prepared by vacuum thermal evaporation contains the metal at least partially in its elemental form.

For the use in consumer electronics, only metals containing stable nuclides or nuclides having very long halftime of radioactive decay might be applicable. As an acceptable level of nuclear stability, the nuclear stability of natural potassium can be taken.

In one embodiment, the n-dopant is selected from electropositive metals selected from alkali metals, alkaline earth metals, rare earth metals and metals of the first transition period Ti, V, Cr and Mn. Preferably, the n-dopant is selected from Li, Na, K, Rb, Cs, Mg, Ca, Sr, Ba, Sm, Eu, Tm, Yb; more preferably from Li, Na, K, Rb, Cs, Mg and Yb, even more preferably from Li, Na, Cs and Yb, most preferably from Li, Na and Yb.

The redox dopant may be essentially non-emissive.

ETL Layer Stack

According to another embodiment, the first and the second matrix compound may be selected different, and wherein
  the first electron transport layer consist of a first matrix compound of formula (I); and
  the second electron transport layer consist of a second matrix compound of formula (II), and an alkali metal salt or an alkali metal organic complex.

Preferably, the first and second electron transport layer may be essentially non-emissive.

According to another embodiment, the first electron transport layer can be in direct contact with the emission layer.

According to another embodiment, the first electron transport layer can be in direct contact with the second electron transport layer.

According to another embodiment, the first electron transport layer can be contacting sandwiched between the emission layer and the second electron transport layer.

According to another embodiment, the second electron transport layer can be in direct contact with the electron injection layer.

According to another embodiment, the second electron transport layer can be contacting sandwiched between the first electron transport layer and the electron injection layer.

According to another embodiment, the second electron transport layer can be in direct contact with the cathode electrode.

According to another embodiment, the second electron transport layer can be contacting sandwiched between the first electron transport layer and the cathode layer.

According to another embodiment, the first electron transport layer can be contacting sandwiched between the emission layer and the second electron transport layer, and the second electron transport layer can be contacting sandwiched between the first electron transport layer and the electron injection layer.

According to another aspect of the invention, it is provided an electronic device comprising at least one organic light emitting device according to any embodiment described throughout this application, preferably, the electronic device comprises the organic light emitting diode in one of embodiments described throughout this application. More preferably, the electronic device is a display device.

Hereinafter, the figures are illustrated in more detail with reference to examples. However, the present disclosure is not limited to the following figures.

Figure 1:
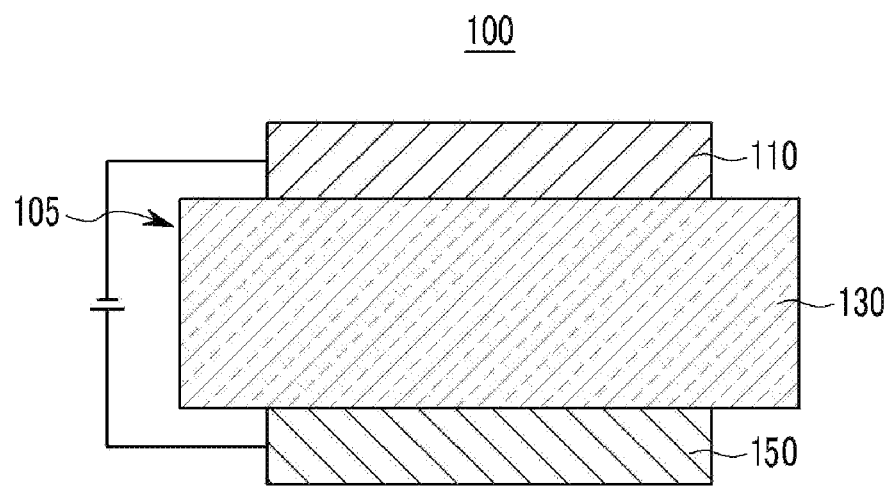
FIG. 1 is a cross-sectional view showing an organic light emitting diode according to an embodiment of the invention.
Figure 2:
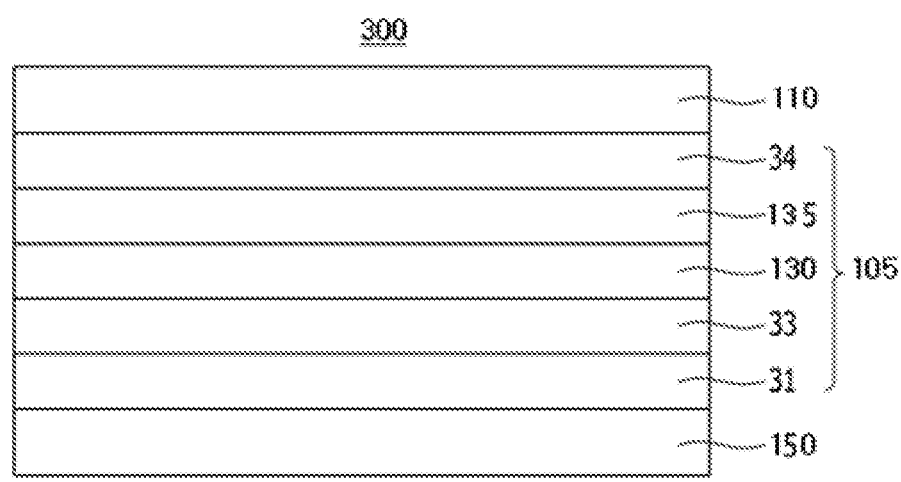
FIGS. 2 and 3 are cross-sectional views specifically showing a part of an organic layer of an organic light emitting diode according to an embodiment of the invention.
Figure 3:
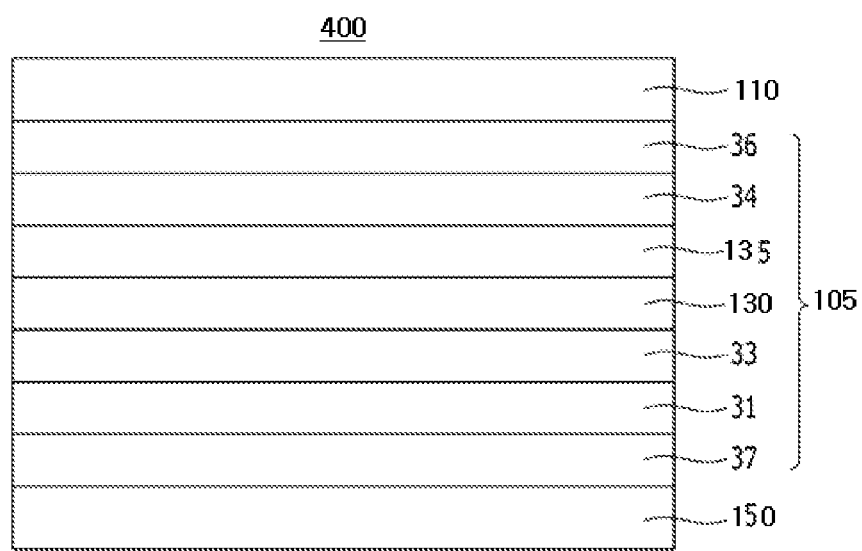

FIGS. 1 to 3 are schematic cross-sectional views of organic light emitting diodes 100, 300, and 400 according to an embodiment of the present invention. Hereinafter, referring to FIG. 1, a structure of an organic light emitting diode according to an embodiment of the present invention and a method of manufacturing the same are as follows. The organic light emitting diode 100 has a structure where an anode 110, a stack of organic layers 105 including an optional hole transport region; an emission layer 130; and a cathode 150 that are sequentially stacked.

A substrate may be disposed on the anode 110 or under the cathode 150. The substrate may be selected from usual substrate used in a general organic light emitting diode and may be a glass substrate or a transparent plastic substrate.

The anode 110 may be formed by depositing or sputtering an anode material on a substrate. The anode material may be selected from materials having a high work function that makes hole injection easy. The anode 110 may be a reflective electrode, a transflective electrode, or a transmissive electrode. The anode material may use indium tin oxide (ITO), indium zinc oxide (IZO), tin oxide ($SnO_2$), zinc oxide (ZnO), and the like. Or, it may be a metal such as silver (Ag), or gold (Au), or an alloy thereof.

The anode 110 may have a monolayer or a multi-layer structure of two or more layers.

The organic light emitting diodes 100, 300, and 400 according to an embodiment of the present invention may include a hole transport region; an emission layer 130; and an first electron transport layer 33 comprising a compound according to formula I.

Referring to FIG. 2, the hole transport region of the stack of organic layers 105 may include at least two layered hole transport layers, and in this case, the hole transport layer contacting the emission layer (130) is defined as a first hole transport layer 135 and a the hole transport layer contacting the anode (110) is defined as a second hole transport layer 34. The stack of organic layers 105 further includes two electron transport layers, namely first electron transport layer 33 and the second electron transport layer 31. The hole transport region of the stack 105 may further include at least one of a hole injection layer, a hole transport layer, an electron blocking layer, and a buffer layer.

The hole transport region of the stack 105 may include only hole injection layer or only hole transport layer. Or, the hole transport region may have a structure where a hole injection layer 36/hole transport layer 34 or hole injection layer 36/hole transport layer 34/electron blocking layer (135) is sequentially stacked from the anode 110.

For example, the hole injection layer 36 and the electron injection layer 37 can be additionally included, so that an OLED may comprises an anode 110/hole injection layer 36/hole transport layer 34/electron blocking layer 135/emission layer 130/first electron transport layer 33/second electron transport layer 31/electron injection layer 37/cathode 150, which are sequentially stacked.

According to another aspect of the invention, the organic electroluminescent device (400) comprises a anode (110), a hole injection layer (36), a hole transport layer (34), optional an electron blocking layer (135), an emission layer (130), first electron transport layer (33), second electron transport layer (31), an optional electron injection layer (37), a cathode (150) wherein the layers are arranged in that order.

The hole injection layer 36 may improve interface properties between ITO as an anode and an organic material used for the hole transport layer 34, and is applied on a non-planarized ITO and thus planarizes the surface of the ITO. For example, the hole injection layer 36 may include a material having a median value of the energy level of its highest occupied molecular orbital (HOMO) between the work function of ITO and the energy level of the HOMO of the hole transport layer 34, in order to adjust a difference between the work function of ITO as an anode and the energy level of the HOMO of the hole transport layer 34.

When the hole transport region includes a hole injection layer 36, the hole injection layer may be formed on the anode 110 by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-6}$ Pa to about $10^{-1}$ Pa, and a deposition rate of about 0.1 to about 10 nm/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

Conditions for forming the hole transport layer and the electron blocking layer may be defined based on the above-described formation conditions for the hole injection layer.

A thickness of the hole transport part of the charge transport region may be from about 10 nm to about 1000 nm, for example, about 10 nm to about 100 nm. When the hole transport transport part of the charge transport region includes the hole injection layer and the hole transport layer, a thickness of the hole injection layer may be from about 10 nm to about 1000 nm, for example about 10 nm to about 100 nm and a thickness of the hole transport layer may be from about 5 nm to about 200 nm, for example about 10 nm to about 150 nm. When the thicknesses of the hole transport part of the charge transport region, the HIL, and the HTL are within these ranges, satisfactory hole transport characteristics may be obtained without a substantial increase in driving voltage.

Hole transport matrix materials used in the hole transport region are not particularly limited. Preferred are covalent compounds comprising a conjugated system of at least 6 delocalized electrons. Typical examples of hole transport matrix materials which are widely used in hole transport layers are polycyclic aromatic hydrocarbons, triaryl amine compounds and heterocyclic aromatic compounds. Suitable ranges of frontier orbital energy levels of hole transport matrices useful in various layer of the hole transport region are well-known. In terms of the redox potential of the redox couple HTL matrix/cation radical of the HTL matrix, the preferred values (if measured for example by cyclic voltammetry against ferrocene/ferrocenium redox couple as reference) may be in the range 0.0-1.0 V, more preferably in the range 0.2-0.7 V, even more preferably in the range 0.3-0.5 V.

The hole transport region of the stack of organic layers may further include a charge-generating material to improve conductivity, in addition to the materials as described above. The charge-generating material may be homogeneously or non-homogeneously dispersed in the hole transport region.

The charge-generating material may be, for example, a p-dopant. The p-dopant may be one of a quinone derivative, a metal oxide, and a cyano group-containing compound, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as compound HT-D1 below.

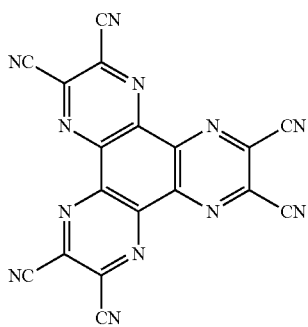

Compound HT-D1

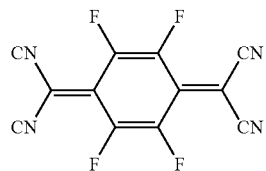

F4-TCNQ

The hole transport part of the charge transport region may further include a buffer layer.

The buffer layer may compensate for an optical resonance distance of light according to a wavelength of the light emitted from the EML, and thus may increase efficiency.

The emission layer (EML) may be formed on the hole transport region by using vacuum deposition, spin coating, casting, LB method, or the like. When the emission layer is formed using vacuum deposition or spin coating, the conditions for deposition and coating may be similar to those for the formation of the hole injection layer, though the conditions for the deposition and coating may vary depending on the material that is used to form the emission layer. The emission layer may include an emitter host (EML host) and an emitter dopant (further only emitter).

The emitter may be a red, green, or blue emitter.

In one embodiment, the emitter host is an anthracene matrix compound represented by formula 400 below:

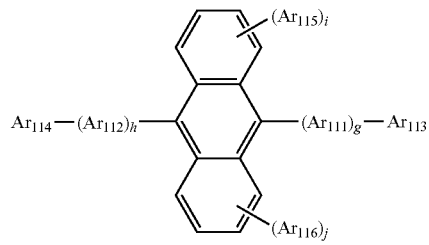

Formula 400

In formula 400, $Ar_{111}$ and $Ar_{112}$ may be each independently a substituted or unsubstituted $C_6$-$C_{60}$ arylene group; $Ar_{113}$ to $Ar_{116}$ may be each independently a substituted or unsubstituted $C_1$-$C_{10}$ alkyl group or a substituted or unsubstituted $C_6$-$C_{60}$ aryl group; and g, h, i, and j may be each independently an integer from 0 to 4. In some embodiments, $Ar_{111}$ and $Ar_{112}$ in formula 400 may be each independently one of a phenylene group, a naphthylene group, a phenanthrenylene group, or a pyrenylene group; or a phenylene group, a naphthylene group, a phenanthrenylene group, a fluorenyl group, or a pyrenylene group, each substituted with at least one of a phenyl group, a naphthyl group, or an anthryl group.

In formula 400, g, h, i, and j may be each independently an integer of 0, 1, or 2. In formula 400, $Ar_{113}$ to $Ar_{116}$ may be each independently one of a $C_1$-$C_{10}$ alkyl group substituted with at least one of a phenyl group, a naphthyl group, or an anthryl group;

a phenyl group, a naphthyl group, an anthryl group, a pyrenyl group, a phenanthrenyl group, or a fluorenyl group;

a phenyl group, a naphthyl group, an anthryl group, a pyrenyl group, a phenanthrenyl group, or a fluorenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or a fluorenyl group; or

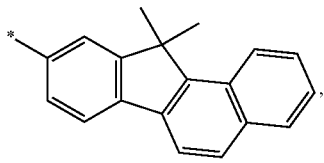

or formulas (Y2) or (Y3)

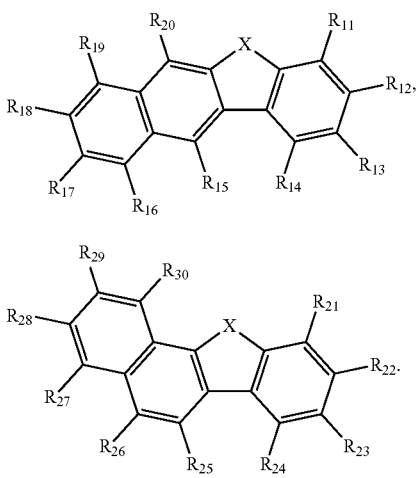

Wherein in the formulas (Y2) and (Y3), X is selected from an oxygen atom and a sulfur atom, but embodiments of the invention are not limited thereto.

In the formula (2Y), any one of $R_{11}$ to $R_{14}$ is used for bonding to $Ar_{111}$. $R_{11}$ to $R_{14}$ that are not used for bonding to $Ar_{111}$ and $R_{15}$ to $R_{20}$ are the same as $R_1$ to $R_8$.

In the formula (3Y), any one of $R_{21}$ to $R_{24}$ is used for bonding to $Ar_{111}$. $R_{21}$ to $R_{24}$ that are not used for bonding to $Ar_{111}$ and $R_{25}$ to $R_{30}$ are the same as $R_1$ to $R_8$.

Preferably, the EML host comprises between one and three heteroatoms selected from the group consisting of N, O or S. More preferred the EML host comprises one heteroatom selected from S or O.

According to a further aspect of the invention, the emitter host respectively has a reduction potential which, if measured under the same conditions by cyclic voltammetry against Fc/Fc$^+$ in tetrahydrofuran, has a value more negative than the respective value obtained for 7-([1,1'-biphenyl]-4-yl)dibenzo[c,h]acridine, preferably more negative than the respective value for 9,9',10,10'-tetraphenyl-2,2'-bianthracene, more preferably more negative than the respective value for 2,9-di([1,1'-biphenyl]-4-yl)-4,7-diphenyl-1,10-phenanthroline, even more preferably more negative than the respective value for 2,4,7,9-tetraphenyl-1,10-phenanthroline, even more preferably more negative than the respective value for 9,10-di(naphthalen-2-yl)-2-phenylanthracene, even more preferably more negative than the respective value for 2,9-bis(2-methoxyphenyl)-4,7-diphenyl-1,10-phenanthroline, most preferably more negative than the respective value for 9,9'-spirobi[fluorene]-2,7-diyl-bis(diphenylphosphine oxide).

The emitter is mixed in a small amount to cause light emission, and may be generally a material such as a metal complex that emits light by multiple excitation into a triplet or more. The emitter may be, for example an inorganic, organic, or organometallic compound, and one or more kinds thereof may be used.

The emitter may be a fluorescent emitter, for example ter-fluorene, the structures are shown below. 4.4'-bis(4-diphenyl amiostyryl)biphenyl (DPAVBi), 2,5,8,11-tetra-tert-butyl perylene (TBPe), and Compound 4 below are examples of fluorescent blue emitters.

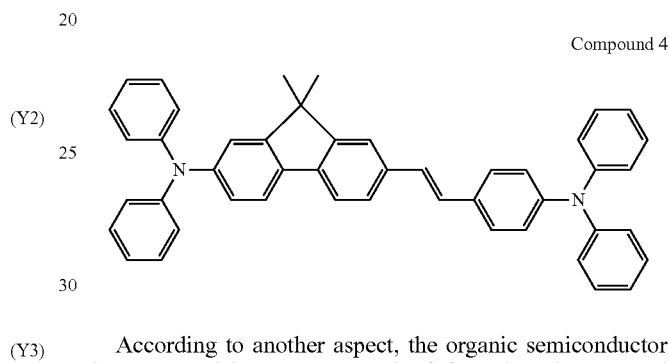

Compound 4

According to another aspect, the organic semiconductor layer comprising a compound of formula I is arranged between a fluorescent blue emission layer and the cathode electrode.

The emitter may be a phosphorescent emitter, and examples of the phosphorescent emitters may be organometallic compounds including Ir, Pt, Os, Ti, Zr, Hf, Eu, Tb, Tm, Fe, Co, Ni, Ru, Rh, Pd, or a combination thereof. The phosphorescent emitter may be, for example a compound represented by formula Z, but is not limited thereto:

$$L_2MX \qquad (Z).$$

In formula Z, M is a metal, and L and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or, in a polynuclear complex, a combination thereof, and the L and X may be, for example, a bidendate ligand.

A thickness of the emission layer may be about 10 nm to about 100 nm, for example about 20 nm to about 60 nm. When the thickness of the emission layer is within these ranges, the emission layer may have improved emission characteristics without a substantial increase in a driving voltage.

Next, the electron transport region of the stack of organic layers 105 may be disposed on the emission layer.

The electron transport region of the stack of organic layers includes at least the first electron transport layer and the second electron transport layer. The electron transport region of the stack of organic layers may further include an electron injection layer.

For example, the electron transport region of the stack of organic layers may have a structure of the first electron transport layer/second electron transport layer/electron injection layer but is not limited thereto. For example, an organic light emitting diode according to an embodiment of the present invention includes at least two electron transport layers in the electron transport region of the stack of organic layers 105, and in this case, the electron transport layer contacting the emission layer is defined as the first electron transport layer 33.

The electron transport layer may include two or more different electron transport matrix compounds.

The formation conditions of the first electron transport layer 33, second electron transport layer 31, and electron injection layer 37 of the electron transport region of the stack of organic layers refer to the formation conditions of the hole injection layer.

The thickness of the first electron transport layer may be from about 2 nm to about 100 nm, for example about 3 nm to about 30 nm. When the thickness of the first electron transport layer is within these ranges, the first electron transport layer may have improved electron transport auxiliary ability without a substantial increase in driving voltage.

A thickness of the second electron transport layer may be about 10 nm to about 100 nm, for example about 15 nm to about 50 nm. When the thickness of the electron transport layer is within these ranges, the electron transport layer may have satisfactory electron transporting ability without a substantial increase in driving voltage.

According to another aspect of the invention, the organic electroluminescent device further comprises an electron injection layer between the second electron transport layer and the cathode.

The electron injection layer (EIL) 37 may facilitate injection of electrons from the cathode 150.

According to another aspect of the invention, the electron injection layer 37 comprises:
(i) an electropositive metal selected from alkali metals, alkaline earth metals and rare earth metals in substantially elemental form, preferably selected from Li, Na, K, Rb, Cs, Mg, Ca, Sr, Ba, Eu and Yb, more preferably from Li, Na, Mg, Ca, Sr and Yb, even more preferably from Li and Yb, most preferably Yb; and/or
(ii) an alkali metal complex and/or alkali metal salt, preferably the Li complex and/or salt, more preferably a Li quinolinolate, even more preferably a lithium 8-hydroxyquinolinolate, most preferably the alkali metal salt and/or complex of the second electron transport layer is identical with the alkali metal salt and/or complex of the injection layer.

The electron injection layer may include at least one selected from LiF, NaCl, CsF, $Li_2O$, and BaO.

A thickness of the EIL may be from about 0.1 nm to about 10 nm, or about 0.3 nm to about 9 nm. When the thickness of the electron injection layer is within these ranges, the electron injection layer may have satisfactory electron injection ability without a substantial increase in driving voltage.

A material for the cathode 150 may be a metal, an alloy, or an electrically conductive compound that have a low work function, or a combination thereof. Specific examples of the material for the cathode 150 may be lithium (Li), magnesium (Mg), aluminum (Al), aluminum-lithium (Al—Li), calcium (Ca), magnesium-indium (Mg—In), magnesium-silver (Mg—Ag), etc. In order to manufacture a top-emission light-emitting device having a reflective anode 110 deposited on a substrate, the cathode 150 may be formed as a transmissive electrode from, for example, indium tin oxide (ITO) or indium zinc oxide (IZO).

Hereinafter, the embodiments are illustrated in more detail with reference to examples. However, the present disclosure is not limited to the following examples.

DETAILED DESCRIPTION

Synthesis and physical properties of compound of formula I

Triazine compounds of formula I may be synthesized in accordance with the methods described in PCT-KR2015-012551.

SYNTHESIS EXAMPLE 1

Compound A6 (in the Scheme Referred as Compound [3])

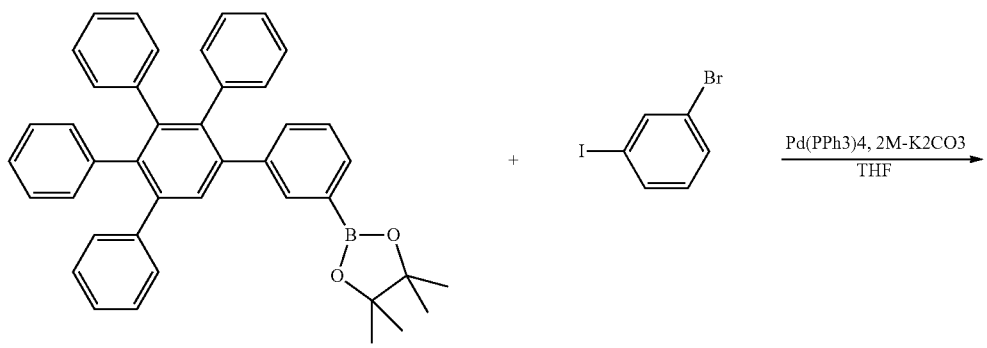

I-4

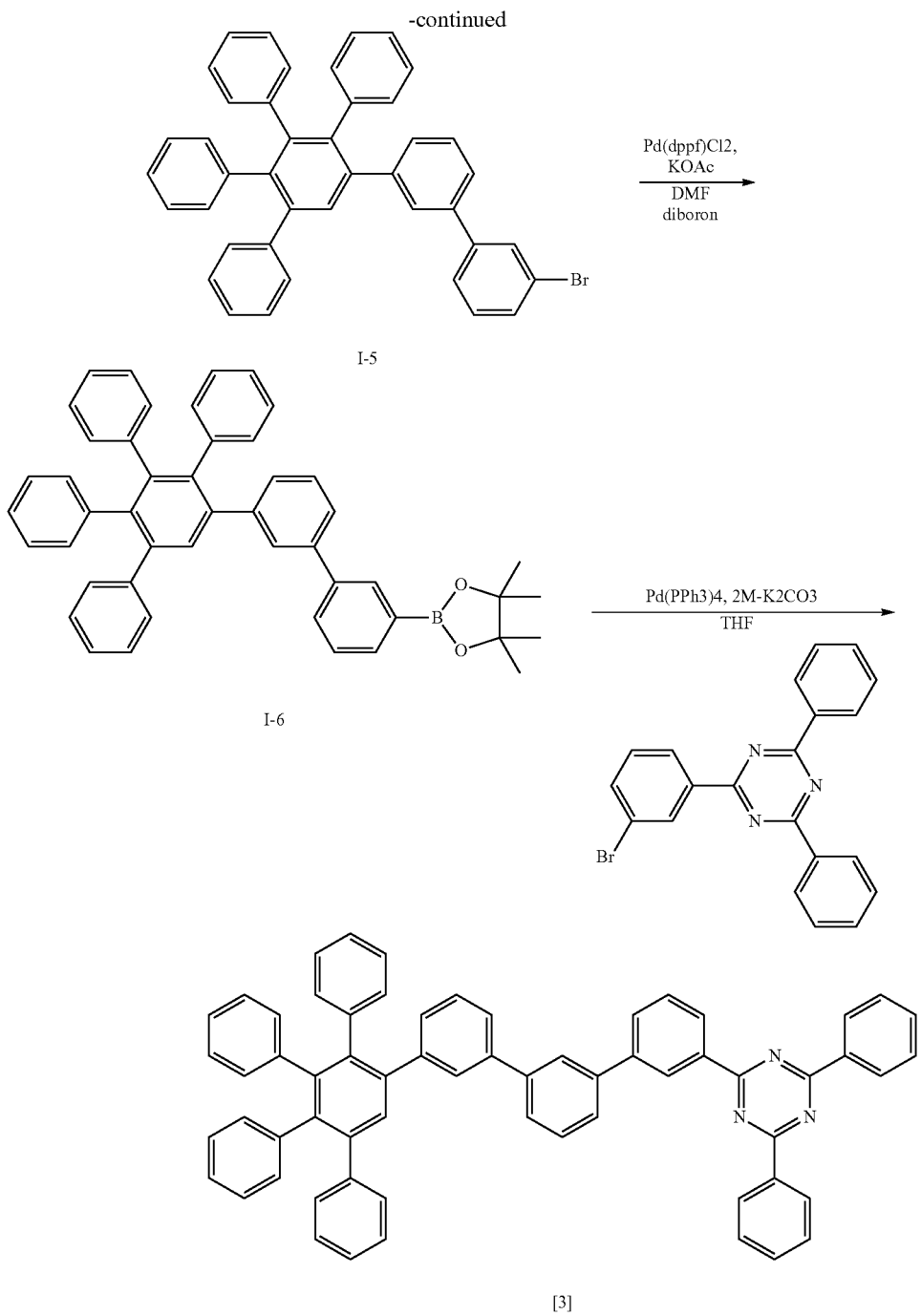

First Step: Synthesis of Intermediate I-5

13 g of an intermediate I-5 (61%) was obtained in the same synthesis method as the synthesis method of the compound 1 by using the intermediate I-4 (20.4 g, 34.92 mmol) and 1-bromo-3-iodobenzene (16.5 g, 52.39 mmol) under a nitrogen environment.

Second Step: Synthesis of Intermediate I-6

10 g of an intermediate I-6 (74%) was obtained in the same synthesis method as the synthesis method of the intermediate I-4 by using the intermediate I-5 (12.6 g, 20.54 mmol) under a nitrogen environment.

Third Step: Synthesis of Compound A6

8.7 g of compound A6 (in the scheme referred as [3]) was obtained in 68% yield by using the intermediate I-6 (10 g, 15.2 mmol) and 2-(3-bromophenyl)-4,6-diphenyl-1,3,5-triazine (7.9 g, 18.32 mmol). These reagents were dissolved in 250 mL tetrahydrofuran under a nitrogen environment, tetrakis(triphenylphosphine)palladium (0.9 g, 0.75 mmol) was added thereto, and the mixture was stirred. Then, potassium carbonate saturated in water (5.2 g, 37 mmol) was added thereto, and the mixture was heated and refluxed at 80° C. for 24 hours. When the reaction was complete, water was added to the reaction solution, dichloromethane was used to perform an extraction, an anhydrous MgSO₄ was used to remove moisture therefrom, and a resultant therefrom was filtered and concentrated under a reduced pressure. This obtained residue was separated and purified through column chromatography.

LC Mass (theoretical value: 842.04 g/mol, measured value: M+H⁺=843.03 g/mol)

The benzoquinazoline compound A9 was prepared analogously. Physical properties of tested compounds of formula (I) are summarized in Table 1.

Dibenzoacridine compounds of formula I may be synthesized in accordance with the methods described in WO2011/154131A1.

Another alternative is demonstrated in Synthesis example 2. The procedure is generally applicable for the synthesis of compounds comprising the hexaphenylbenzene structural moiety.

SYNTHESIS EXAMPLE 2

Compound A16

Step 1: Synthesis of 7-(4-(phenylethynyl)phenyl)dibenzo[c,h]acridine

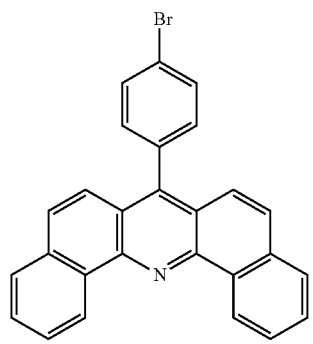

A three necked 250-mL round bottom flask is purged with $N_2$. Under a constant flow of $N_2$ 7-(4-bromophenyl)dibenzo[c,h]acridine (10.0 g, 23.0 mmol), phenylacetylene (4.70 g, 46.0 mmol, 2.0 eq.), and bis (triphenylphosphine)-palladium chloride (3.23 g, 4.6 mmol, 0.2 eq.) were introduced, followed by a 1M-solution of tetrabutylammonium fluoride in THF (70 mL). The resulting mixture was warmed up to reflux and reacted for 2 h. After completion of the reaction, MeOH (70 mL) was added, and the solution was left to cool down to room temperature. The precipitate formed upon cooling was collected by filtration, washed with MeOH (2×50 mL), then hexane (3×50 mL), and finally dried under vacuum at 40° C.

Yield: about 7.0 g (about 67%, yellowish solid).

Step 2: Synthesis of 7-(3',4',5',6'-tetraphenyl-[1,1':2',1''-terphenyl]-4-yl)dibenzo[c,h]acridine

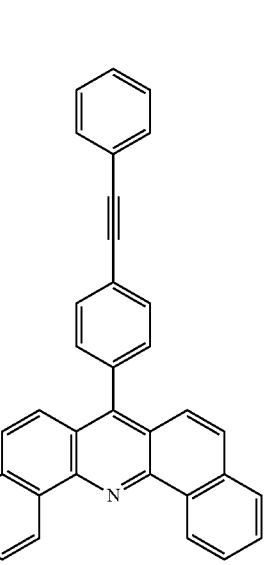

A three necked 100-mL round bottom flask was charged with 7-(4-(phenylethynyl)phenyl)dibenzo[c,h]acridine (6.8 g, 14.9 mmol), 2,3,4,5-tetraphenylcyclopenta-2,4-dienone (6.31 g, 16.4 mmol, 1.1 eq.), and benzophenone (35 g as molten solvent). After degassing the solids with $N_2$, the resulting mixture was warmed up to 300° C. After 1 h of reflux at 300° C., gas evolution had stopped and the mixture was hence cooled down to ca. 80° C. Toluene (100 mL), was added, and the resulting precipitate was filtered off and washed with toluene (2×40 mL), followed by hexane (2×40 mL). The solid was then purified by trituration in hot chlorobenzene (60 mL), followed by trituration in hot MeOH (60 mL). After filtration and drying under vacuum at 120° C., the desired was isolated as a yellowish powder.

Yield: about 6.8 g (about 56%, yellowish solid).

The benzoacridine compound A18 was prepared analogously. In Table 1 are summarized dibenzoacridine compounds of formula I and their starting material, yield, m/z, glass transition temperature, reduction potential against $Fc/Fc^+$ in tetrahydrofuran.

TABLE 1

| Comp. I: | Starting materials | Structure of compound I | Yield [%] | Tg [° C.] | Redox potential against $Fc/Fc^+$ [V] |
|---|---|---|---|---|---|
| A1 | | | 62% | 175 | −2.25 |
| A2 | | | | 138 | −2.20 |
| A3 | | | | 135 | −2.20 |

TABLE 1-continued
| Comp. I: | Starting materials | Structure of compound I | Yield [%] | Tg [° C.] | Redox potential against Fc/Fc+ [V] |
|---|---|---|---|---|---|
| A4 | | 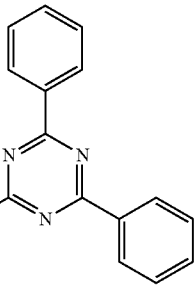 | | 140 | −2.22 |
| A5 | 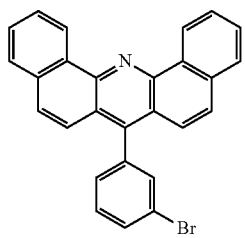 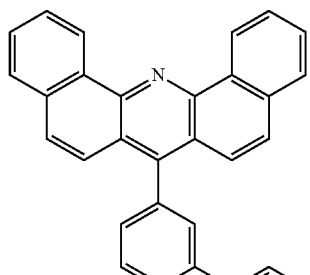 | 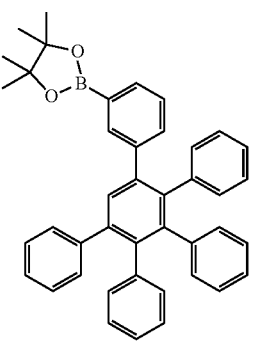 | 86% | 165 | −2.29 |
| A6 | | 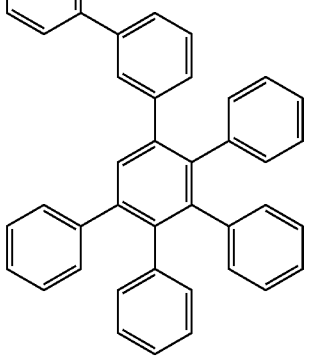 | | 139 | −2.18 |

TABLE 1-continued
| Comp. I: | Starting materials | Structure of compound I | Yield [%] | Tg [° C.] | Redox potential against Fc/Fc+ [V] |
|---|---|---|---|---|---|
| A7 | | 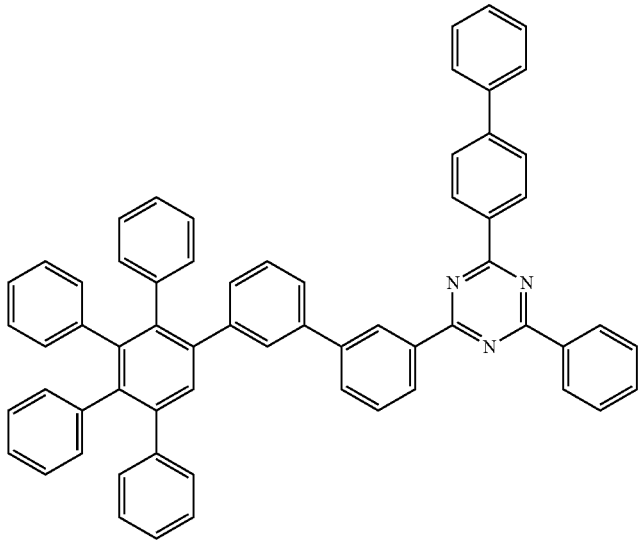 | | 147 | −2.15 |
| A8 | | 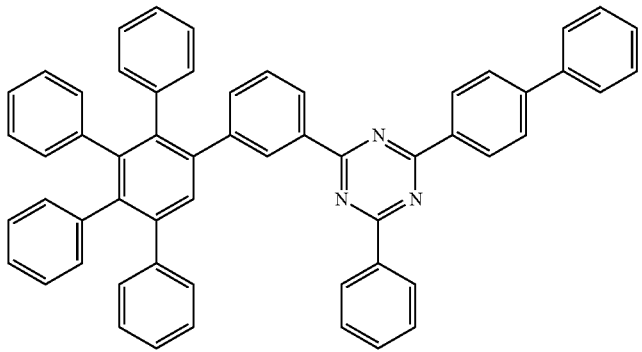 | | 147 | −2.18 |
| A9 | | 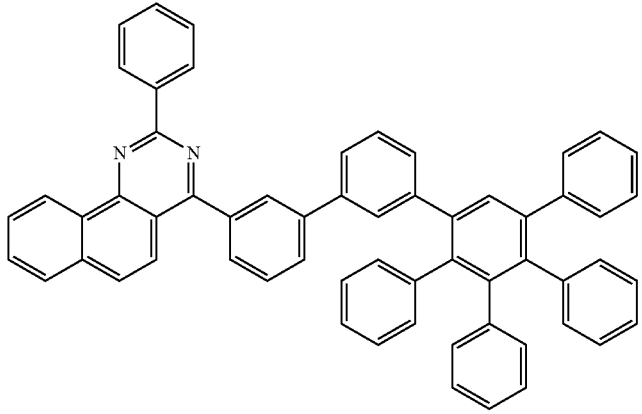 | | 144 | −2.25 |

TABLE 1-continued
| Comp. I: | Starting materials | Structure of compound I | Yield [%] | Tg [° C.] | Redox potential against Fc/Fc+ [V] |
|---|---|---|---|---|---|
| A10 | | 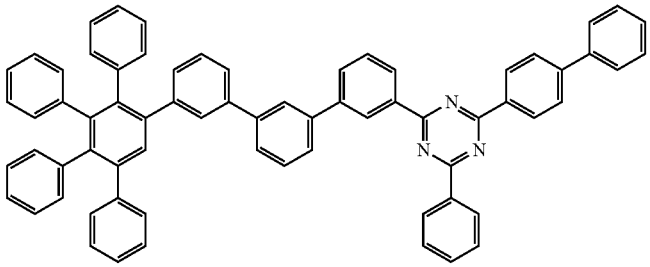 | | 149 | −2.14 |
| A12 | | 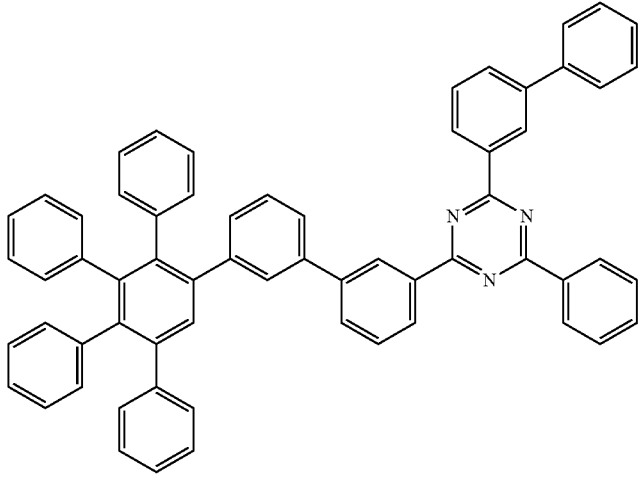 | | — | −2.18 |
| A13 | | 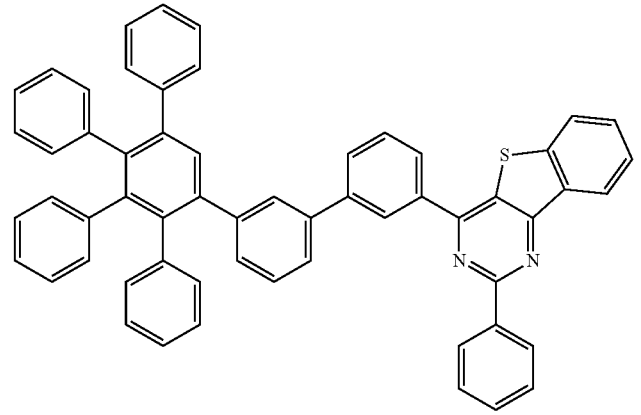 | | — | −2.23 |

TABLE 1-continued

| Comp. I: | Starting materials | Structure of compound I | Yield [%] | Tg [° C.] | Redox potential against Fc/Fc+ [V] |
|---|---|---|---|---|---|
| A15 | | | 58% | 159 | −2.29 |
| A16 | | | | | −2.31 |

TABLE 1-continued
| Comp. I: | Starting materials | Structure of compound I | Yield [%] | Tg [° C.] | Redox potential against Fc/Fc+ [V] |
|---|---|---|---|---|---|
| A17 | 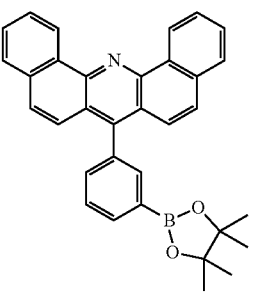 [SMILES: CC1(C)OB(c2cccc(-c3c4ccc5ccccc5c4nc4c3ccc3ccccc34)c2)OC1(C)C] | 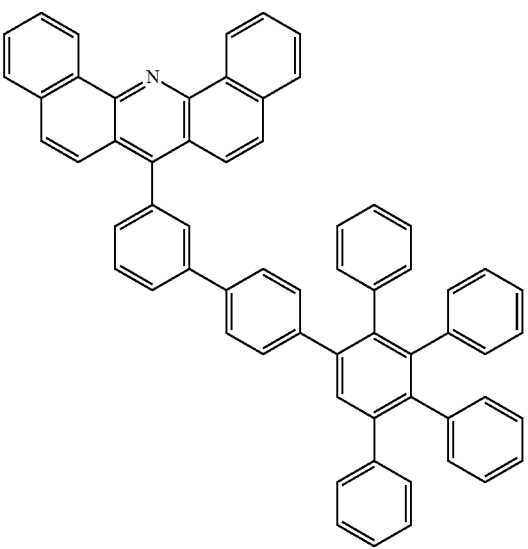 [SMILES: c1ccc(-c2cc(-c3ccc(-c4cccc(-c5c6ccc7ccccc7c6nc6c5ccc5ccccc56)c4)cc3)c(-c3ccccc3)c(-c3ccccc3)c2-c2ccccc2)cc1] | 50% | 175 | — |
| A18 | | 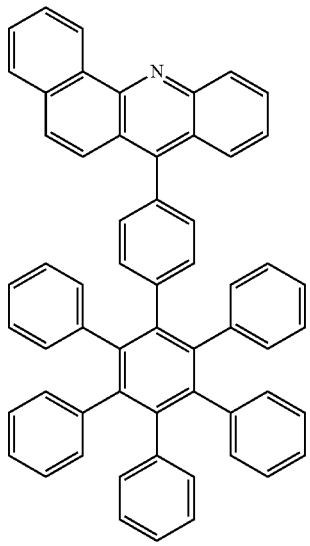 [SMILES: c1ccc(-c2c(-c3ccccc3)c(-c3ccccc3)c(-c3ccc(-c4c5ccccc5nc5c4ccc4ccccc45)cc3)c(-c3ccccc3)c2-c2ccccc2)cc1] | Not observed | | −2.25 |

General Procedure for Fabrication of OLEDs

The model bottom emitting blue fluorescent OLED is described below.

It was prepared using auxiliary materials F1, F2, F3, F4 and PD-2:

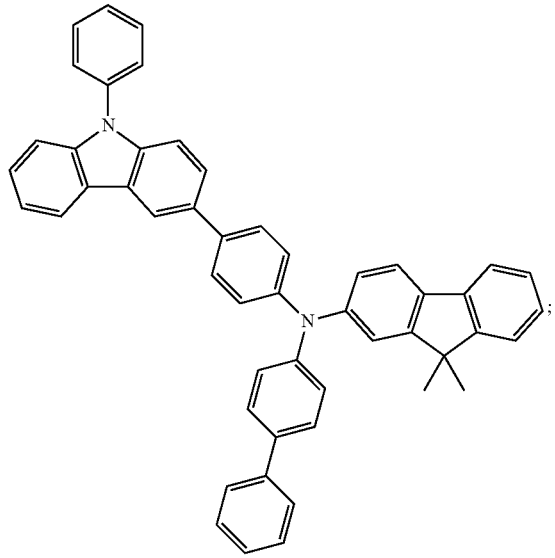

biphenyl-4-yl(9,9-diphenyl-9H-fluoren-2-yl)-[4-(9-phenyl-9H-carbazol-3-yl)phenyl]-amine, CAS 1242056-42-3, F1

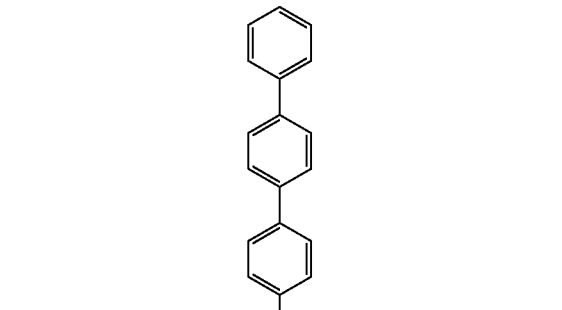

N,N-bis(4-(dibenzo[b,d]furan-4-yl)phenyl)-[1,1′:4,1″-terphenyl]-4-amine, CAS 1198399-61-9, F2

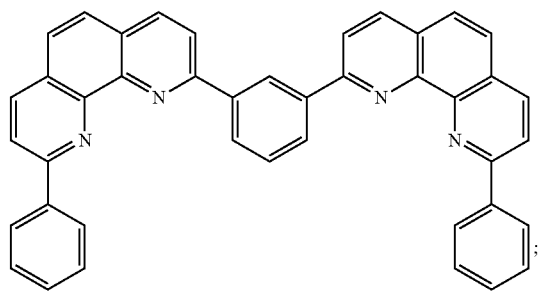

1,3-bis(9-phenyl-1,10-phenanthrolin-2-yl)benzene, CAS 721969-94-4, F3

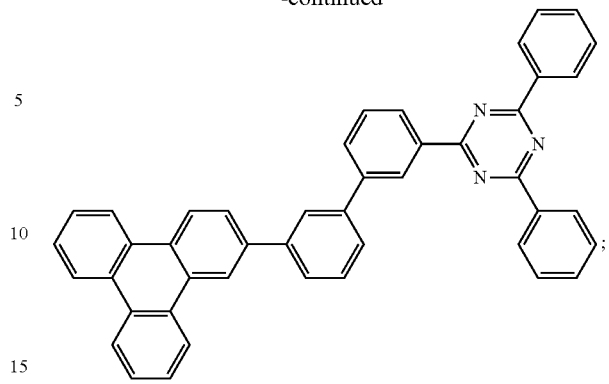

2,4-diphenyl-6-(3′-triphenylen-2-yl)-[1,1′-bihenyl]-3-yl)-1,3,5-triazine, CAS 1638271-85-8, F4

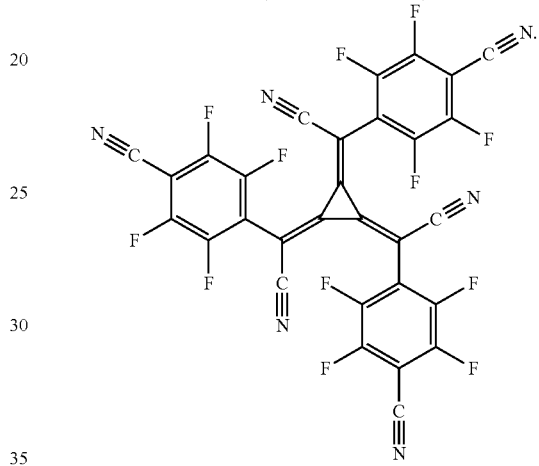

2,2′,2″-(cyclopropane-1,2,3-triylidene)tris(2-(p-cyanotetrafluorophenyl)acetonitrile), CAS 1224447-88-4, PD-2

DEVICE EXAMPLE 1

Bottom Emitting Blue OLED

The blue emitting device was made by depositing a 5 nm layer of F1 doped with PD2 (matrix to dopant weight ratio of 92:8 wt %) onto an ITO-glass substrate, followed by a 125 nm undoped layer of F1 and 10 nm undoped layer of F2. Subsequently, a blue fluorescent emitting layer of ABH113 (Sun Fine Chemicals) doped with BD200 (Sun Fine Chemicals) (97:3 wt %) was deposited with a thickness of 25 nm. A 15 or 20 nm thick interlayer of the tested compound and 15 or 10 nm layer of F3 doped with elemental lithium (99.5:0.5 wt %) were deposited subsequently on the emitting layer. Finally, an aluminium layer with a thickness of 100 nm was deposited as a cathode on top of the metal-doped layer.

The OLED stack may be protected from ambient conditions by encapsulation of the device with a glass slide. Thereby, a cavity is formed, which includes a getter material for further protection.

Evaluation of Device Experiments

To assess the performance of the inventive examples compared to the prior art, the current efficiency is measured under ambient conditions (20° C.). Operational voltage measurements are performed using a Keithley 2400 sourcemeter, and reported in V at standard current density 10 mA/cm² for top emission devices. For bottom emission devices, the standard current density is usually 15 mA/cm². A calibrated spectrometer CAS140 from Instrument Systems is used for measurement of CIE coordinates and brightness in Candela. Lifetime LT of the device is measured at ambient conditions (20° C.) and standard current density 10 mA/cm² or 15 mA/cm², using a Keithley 2400 sourcemeter, and recorded in hours. The brightness of the device is measured using a calibrated photo diode. The lifetime LT is defined as the time till the brightness of the device is reduced to 97% of its initial value.

The light output in external efficiency EQE and power efficiency $P_{eff}$ (1 m/W) are determined at 10 mA/cm² for top emission devices.

To determine the efficiency EQE in % the light output of the device is measured using a calibrated photodiode.

To determine the power efficiency in 1 m/W, in a first step the luminance in candela per square meter (cd/m²) is measured with an array spectrometer CAS140 CT from Instrument Systems which has been calibrated by Deutsche Akkreditierungsstelle (DAkkS). In a second step, the luminance is then multiplied by π and divided by the voltage and current density.

In bottom emission devices, the emission is predominately Lambertian and quantified in percent external quantum efficiency (EQE) and power efficiency in 1 m/W.

The auxiliary compound F4 served as a state-of-art reference; the results in terms of colour coordinates x and y, operational voltage, luminance current efficiency $C_{eff}$, power efficiency $P_{eff}$ and quantum efficiency $Q_{eff}$ are shown in Table 2.

The invention claimed is:
1. An organic electroluminescent device comprising an anode, a cathode, an emission layer arranged between the anode and the cathode, a first electron transport layer comprising a first electron transport matrix, a second electron transport layer comprising a second electron transport matrix and a redox n-dopant, wherein the first electron transport layer and the second electron transport layer are arranged between the emission layer and the cathode, wherein the first electron transport layer is arranged closer to the emission layer than the second electron transport layer and the second electron transport layer is arranged closer to the cathode than the first electron transport layer; wherein at least the first electron transport matrix comprises a matrix compound according to Chemical Formula I:

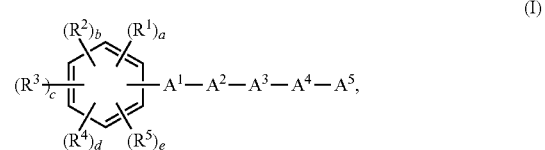

wherein
$A^1$, $A^2$, $A^3$ and $A^4$ is independently selected from single bond, an unsubstituted or substituted $C_6$ to $C_{30}$ arylene and an unsubstituted or substituted $C_1$ to $C_{30}$ heteroarylene;
$A^5$ is selected from an unsubstituted or substituted $C_6$ to $C_{40}$ aryl group and/or from an unsubstituted or substituted $C_2$ to $C_{40}$ heteroaryl group;

TABLE 2

| 1st ETL thickness (nm) | Compound (I) | CIE 1931 x | CIE 1931 y | Voltage/V [15 mA/cm²] | Luminance/(cd/m²) [10 mA/cm²] | $C_{Eff}$/(cd/A) [15 mA/cm²] | $P_{Eff}$/(lm/W) [15 mA/cm²] | $Q_{Eff}$/(lm/W) [15 mA/cm²] |
|---|---|---|---|---|---|---|---|---|
| 15 | A1 | 0.139 | 0.105 | 4.183 | 946 | 9.30 | 6.99 | 9.89 |
| 20 | A2 | 0.137 | 0.110 | 4.005 | 843 | 8.61 | 6.75 | 8.95 |
| 20 | A3 | 0.137 | 0.111 | 4.074 | 949 | 9.49 | 7.32 | 9.75 |
| 20 | A4 | 0.137 | 0.113 | 4.117 | 932 | 9.53 | 7.27 | 9.72 |
| 15 | A5 | 0.139 | 0.106 | 4.027 | 857 | 8.63 | 6.73 | 9.07 |
| 15 | A6 | 0.138 | 0.108 | 4.310 | 955 | 9.40 | 6.85 | 9.77 |
| 15 | A7 | 0.138 | 0.108 | 4.299 | 897 | 8.87 | 6.48 | 9.20 |
| 20 | A8 | 0.136 | 0.116 | 4.329 | 970 | 9.57 | 6.94 | 9.51 |
| 15 | A9 | 0.139 | 0.104 | 4.239 | 826 | 8.83 | 6.54 | 9.48 |
| 20 | A10 | 0.136 | 0.117 | 4.456 | 967 | 9.55 | 6.73 | 9.46 |
| 15 | F4 | 0.138 | 0.108 | 4.208 | 874 | 8.62 | 6.44 | 9.01 |

Technical Effect of the Invention

As it may be taken from the Table 2, a majority of the tested compounds of formula (I) implemented in a state-of-art blue OLED comprising redox doped second ETL and redox doped HTL showed better results (results in boldface letters) than the state-of-art matrix compound F4 used as reference. Most impressive is the improvement in power efficiency which was achieved in all tested compounds.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

$R^1$ to $R^5$ are independently a substituted or unsubstituted $C_6$ to $C_{30}$ aryl group, a substituted or unsubstituted $C_2$ to $C_{30}$ heteroaryl group;
a to e are independently an integer of 0 or 1 and 4≤a+b+c+d+e≤5; and
wherein in the substituted group, at least one hydrogen is replaced by
(i) deuterium,
(ii) a halogen,
(iii) a $C_2$ to $C_{60}$ tertiary amino group, wherein the nitrogen atom of the tertiary amino group is substituted with two independently selected $C_1$ to $C_{30}$ hydrocarbyl groups or the nitrogen atom of the $C_2$ to $C_{60}$ tertiary amino group forms a $C_1$ to $C_{30}$ heterocyclic group,
(iv) a $C_2$ to $C_{60}$ phosphine oxide group, wherein the phosphorus atom of the phosphine oxide group is substituted with two $C_1$ to $C_{30}$ groups independently selected from hydrocarbyl, halogenated hydrocarbyl and hydrocarbyloxy or the phosphorus atom of the phosphine oxide group forms a $C_1$ to $C_{30}$ heterocyclic group,
(v) a $C_1$ to $C_{22}$ silyl group,
(vi) a $C_1$ to $C_{30}$ alkyl group,
(vii) a $C_1$ to $C_{10}$ alkylsilyl group,
(viii) a $C_6$ to $C_{22}$ arylsilyl group,
(ix) a $C_3$ to $C_{30}$ cycloalkyl group,
(x) a $C_2$ to $C_{30}$ heterocycloalkyl group,
(xi) a $C_6$ to $C_{30}$ aryl group,
(xii) a $C_2$ to $C_{30}$ heteroaryl group,
(xiii) a $C_1$ to $C_{20}$ alkoxy group,
(xiv) a $C_1$ to $C_{30}$ perfluoro-hydrocarbyl group,
(xv) a $C_1$ to $C_{10}$ trifluoroalkyl group, or
(xvi) a cyano group, and
the redox dopant is
a) an elemental electropositive metal selected from an alkali metal, an alkaline earth metal, a rare earth metal, a transition metal, or a combination thereof, wherein the transition metal is selected from the group consisting of Ti, V, Cr, and Mn; and/or
b) an electrically neutral metal complex having redox potential which has a value which is more negative than −1.7 V, if measured by cyclic voltammetry against ferrocene/ferrocenium reference redox couple; and/or
c) an electrically neutral organic radical having redox potential which has a value which is more negative than −1.7 V, if measured by cyclic voltammetry against ferrocene/ferrocenium reference redox couple.

2. The organic electroluminescent device according to claim 1, wherein the matrix compound (I) is a compound according to Chemical Formula (Ia)

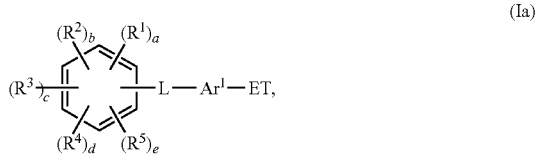

(Ia)

wherein, in Chemical Formula Ia,
$Ar^1$ is selected from $C_6$ to $C_{12}$ arylene and $C_1$ to $C_{11}$ heteroarylene;
$R^1$ to $R^5$ are independently a substituted or unsubstituted C6 to C30 aryl group, a substituted or unsubstituted $C_2$ to $C_{30}$ heteroaryl group;
a to e are independently an integer of 0 or 1 and $4 \leq a+b+c+d+e \leq 5$;
L is a single bond, a substituted or unsubstituted $C_6$ to $C_{30}$ arylene group, or a substituted or unsubstituted $C_2$ to $C_{30}$ heteroarylene group;
ET is a unsubstituted $C_6$ to $C_{40}$ aryl or a unsubstituted $C_5$ to $C_{40}$ heteroaryl group, or a substituted $C_6$ to $C_{40}$ aryl or a substituted $C_5$ to $C_{40}$ heteroaryl group; and
wherein in the substituted group, at least one hydrogen is replaced by
(i) deuterium,
(ii) a halogen,
(iii) a $C_2$ to $C_{60}$ tertiary amino group, wherein the nitrogen atom of the $C_2$ to $C_{60}$ tertiary amino group is substituted with two independently selected $C_1$ to $C_{30}$ hydrocarbyl groups or forms a $C_1$ to $C_{30}$ heterocyclic group,
(iv) a $C_2$ to $C_{60}$ phosphine oxide group, wherein the phosphorus atom of the phosphine oxide group is substituted with two $C_1$ to $C_{30}$ groups independently selected from hydrocarbyl, halogenated hydrocarbyl and hydrocarbyloxy or the phosphorus atom of the phosphine oxide group forms a $C_1$ to $C_{30}$ heterocyclic group,
(v) a $C_1$ to $C_{22}$ silyl group,
(vi) a $C_1$ to $C_{30}$ alkyl group,
(vii) a $C_1$ to $C_{10}$ alkylsilyl group,
(viii) a $C_6$ to $C_{22}$ arylsilyl group,
(ix) a $C_3$ to $C_{30}$ cycloalkyl group,
(x) a $C_2$ to $C_{30}$ heterocycloalkyl group,
(xi) a $C_6$ to $C_{30}$ aryl group,
(xii) a $C_2$ to $C_{30}$ heteroaryl group,
(xiii) a $C_1$ to $C_{20}$ alkoxy group,
(xiv) a $C_1$ to $C_{30}$ perfluoro-hydrocarbyl group,
(xv) a $C_1$ to $C_{10}$ trifluoroalkyl group, or
(xvi) a cyano group.

3. The organic electroluminescent device according to claim 1, wherein the matrix compound (I) is a compound according to Chemical Formula (Ib)

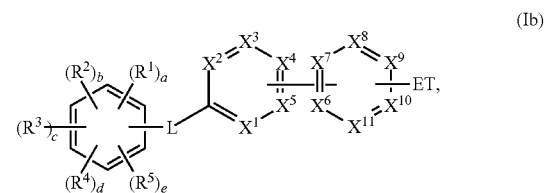

(Ib)

wherein in Chemical Formula Ib:
$X^1$ to $X^{11}$ are independently, N, C, or $CR^a$;
$R^a$ is independently, hydrogen, deuterium, a $C_1$ to $C_{30}$ alkyl group, a $C_3$ to $C_{30}$ cycloalkyl group, a $C_6$ to $C_{30}$ aryl group, a $C_6$ to $C_{30}$ diarylamine group, a $C_1$ to $C_{30}$ alkoxy group, a $C_3$ to $C_{21}$ silyl group, a $C_3$ to $C_{21}$ silyloxy group, a $C_1$ to $C_{30}$ alkylthiol group, a $C_6$ to $C_{30}$ arylthiol group, a halogen, a $C_1$ to $C_{30}$ halogenated hydrocarbyl group, a cyano group;
$R^1$ to $R^5$ are independently a substituted or unsubstituted $C_6$ to $C_{30}$ aryl group, a substituted or unsubstituted $C_2$ to $C_{30}$ heteroaryl group;
a to e are independently an integer of 0 or 1 and $4 \leq a+b+c+d+e \leq 5$;
L is a single bond, a substituted or unsubstituted $C_6$ to $C_{30}$ arylene group, a substituted or unsubstituted $C_2$ to $C_{30}$ heteroarylene group;
ET is a unsubstituted $C_6$ to $C_{40}$ aryl or a unsubstituted $C_2$ to $C_{40}$ heteroaryl group, or a substituted $C_6$ to $C_{40}$ aryl or a substituted $C_2$ to $C_{40}$ heteroaryl group; and
wherein in the substituted group, at least one hydrogen is replaced by
(i) deuterium,
(ii) a halogen,
(iii) a $C_1$ to $C_{60}$ tertiary amino group, wherein the nitrogen atom of the $C_2$ to $C_{60}$ tertiary amino group is substituted with two independently selected $C_1$ to $C_{30}$ hydrocarbyl groups or forms a $C_1$ to $C_{30}$ heterocyclic group,
(iv) a $C_2$ to $C_{60}$ phosphine oxide group, wherein the phosphorus atom of the phosphine oxide group is substituted with two $C_1$ to $C_{30}$ groups independently selected from hydrocarbyl, halogenated hydrocarbyl and hydrocarbyloxy or the phosphorus atom of the phosphine oxide group forms a $C_1$ to $C_{30}$ heterocyclic group,
(v) a $C_1$ to $C_{22}$ silyl group,
(vi) a $C_1$ to $C_{30}$ alkyl group,
(vii) a $C_1$ to $C_{10}$ alkylsilyl group,
(viii) a $C_6$ to $C_{22}$ arylsilyl group,
(ix) a $C_3$ to $C_{30}$ cycloalkyl group,
(x) a $C_2$ to $C_{30}$ heterocycloalkyl group,
(xi) a $C_6$ to $C_{30}$ aryl group,
(xii) a $C_2$ to $C_{30}$ heteroaryl group,
(xiii) a $C_1$ to $C_{20}$ alkoxy group,
(xiv) a $C_1$ to $C_{30}$ perfluoro-hydrocarbyl group,
(xv) a $C_1$ to $C_{10}$ trifluoroalkyl group, or
(xvi) a cyano group.

4. The organic electroluminescent device according to claim 1, wherein the compound (I) is a compound according to formula (Ic)

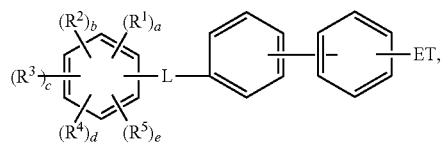

wherein in formula Ic:
$R^1$ to $R^5$ are independently a substituted or unsubstituted $C_6$ to $C_{30}$ aryl group, a substituted or unsubstituted $C_2$ to $C_{30}$ heteroaryl group;
a to e are independently an integer of 0 or 1 and $4 \leq a+b+c+d+e \leq 5$,
L is a single bond, a substituted or unsubstituted $C_6$ to $C_{30}$ arylene group, a substituted or unsubstituted $C_2$ to $C_{30}$ heteroarylene group, and
ET is a unsubstituted $C_6$ to $C_{40}$ aryl or a unsubstituted $C_2$ to $C_{40}$ heteroaryl group, or a substituted $C_6$ to $C_{40}$ aryl or a substituted $C_2$ to $C_{40}$ heteroaryl group; and
wherein in the substituted group, at least one hydrogen is replaced by
(i) deuterium,
(ii) a halogen,
(iii) a $C_1$ to $C_{60}$ tertiary amino group, wherein the nitrogen atom of the $C_2$ to $C_{60}$ tertiary amino group is substituted with two independently selected $C_1$ to $C_{30}$ hydrocarbyl groups or forms a $C_1$ to $C_{30}$ heterocyclic group,
(iv) a $C_2$ to $C_{60}$ phosphine oxide group, wherein the phosphorus atom of the phosphine oxide group is substituted with two $C_1$ to $C_{30}$ groups independently selected from hydrocarbyl, halogenated hydrocarbyl and hydrocarbyloxy or the phosphorus atom of the phosphine oxide group forms a $C_1$ to $C_{30}$ heterocyclic group
(v) a $C_1$ to $C_{22}$ silyl group,
(vi) a $C_1$ to $C_{30}$ alkyl group,
(vii) a $C_1$ to $C_{10}$ alkylsilyl group,
(viii) a $C_6$ to $C_{22}$ arylsilyl group,
(ix) a $C_3$ to $C_{30}$ cycloalkyl group,
(x) a $C_2$ to $C_{30}$ heterocycloalkyl group,
(xi) a $C_6$ to $C_{30}$ aryl group,
(xii) a $C_2$ to $C_{30}$ heteroaryl group,
(xiii) a $C_1$ to $C_{20}$ alkoxy group,
(xiv) a $C_1$ to $C_{30}$ perfluoro-hydrocarbyl group,
(xv) a $C_1$ to $C_{10}$ trifluoroalkyl group, or
(xvi) a cyano group.

5. The organic electroluminescent device according to claim 2, wherein the ET group is a $C_2$ to $C_{30}$ heteroaryl group.

6. The organic electroluminescent device according to claim 2, wherein the ET group includes at least one N, with the proviso that ET is not a carbazolyl group.

7. The organic electroluminescent device according to claim 1, wherein the second electron transport matrix comprises a heterocyclic group containing at least one nitrogen atom and/or the second electron transport matrix comprises at least one phosphine oxide group.

8. The organic electroluminescent device according to claim 1, which is an organic light emitting diode.

9. An electronic device comprising the organic electroluminescent device according to claim 1.

10. The electronic device according to claim 9, wherein the electronic device is a display device.

11. The electronic device according to claim 9, wherein the display device comprises the organic light emitting diode according to claim 8.

\* \* \* \* \*